(12) United States Patent
Medhekar

(10) Patent No.: US 11,406,966 B2
(45) Date of Patent: Aug. 9, 2022

(54) HETEROGENEOUS CATALYST PROCESS AND NICKEL CATALYST

(71) Applicant: INV Nylon Chemicals Americas, LLC, Wilmington, DE (US)

(72) Inventor: Vinay Medhekar, Beaumont, TX (US)

(73) Assignee: INV Nylon Chemicals Americas, LLC, Wilmington, DE (US)

( * ) Notice: Subject to any disclaimer, the term of this patent is extended or adjusted under 35 U.S.C. 154(b) by 868 days.

(21) Appl. No.: 16/093,211

(22) PCT Filed: Apr. 19, 2017

(86) PCT No.: PCT/US2017/028334
§ 371 (c)(1),
(2) Date: Oct. 12, 2018

(87) PCT Pub. No.: WO2017/184710
PCT Pub. Date: Oct. 26, 2017

(65) Prior Publication Data
US 2021/0187484 A1 Jun. 24, 2021

Related U.S. Application Data

(60) Provisional application No. 62/326,148, filed on Apr. 22, 2016.

(51) Int. Cl.
*B01J 23/755* (2006.01)
*B01J 25/02* (2006.01)
(Continued)

(52) U.S. Cl.
CPC ............ *B01J 23/755* (2013.01); *B01J 25/02* (2013.01); *B01J 35/006* (2013.01);
(Continued)

(58) Field of Classification Search
CPC ...... B01J 23/755; B01J 25/02; B01J 35/0053; B01J 35/006; B01J 35/1009;
(Continued)

(56) References Cited

U.S. PATENT DOCUMENTS 1,628,190 A  5/1927  Murray
2,000,171 A  5/1935  Martin
(Continued)

FOREIGN PATENT DOCUMENTS

CN  105148999 A  12/2015
CN  107073586 A  8/2017
(Continued)

OTHER PUBLICATIONS

International Search Report and Written Opinion received for PCT Application No. PCT/US2017/028334, dated Jul. 28, 2017, 10 pages.

(Continued)

*Primary Examiner* — Patricia L. Hailey

(57) ABSTRACT

The present invention relates to heterogeneous catalysts and methods of making and using the same. In various embodiments, the present invention provides a method of making a hydrogenation catalyst including particulate nickel metal (Ni(0)). The method includes calcining first nickel(II)-containing particles in an atmosphere including oxidizing constituents to generate second nickel(II)-containing particles. The method also includes reducing the second nickel(II)-containing particles in a reducing atmosphere while rotating or turning the second nickel(II)-containing particles at about 275° C. to about 360° C. for a time sufficient to generate the particulate nickel metal (Ni(0)), wherein the particulate nickel metal (Ni(0)) is free flowing.

20 Claims, 4 Drawing Sheets

(51) Int. Cl.
*B01J 35/00* (2006.01)
*B01J 35/02* (2006.01)
*B01J 35/10* (2006.01)
*B01J 37/08* (2006.01)
*B01J 37/14* (2006.01)
*B01J 37/18* (2006.01)

(52) U.S. Cl.
CPC ......... *B01J 35/0053* (2013.01); *B01J 35/023* (2013.01); *B01J 35/1009* (2013.01); *B01J 35/1014* (2013.01); *B01J 35/1019* (2013.01); *B01J 37/088* (2013.01); *B01J 37/14* (2013.01); *B01J 37/18* (2013.01)

(58) Field of Classification Search
CPC .. B01J 35/1014; B01J 35/1019; B01J 37/088; B01J 37/14; B01J 37/18; B01J 37/20; C01P 2002/60; C01P 2004/64; C01P 2004/51; C01P 2006/12
USPC ........ 502/337; 585/250, 446, 616, 639, 654; 208/133, 138, 143, 208 R, 209, 217, 208/262.1
See application file for complete search history.

(56) References Cited

U.S. PATENT DOCUMENTS

| | | | |
|---|---|---|---|
| 3,656,934 A | 4/1972 | Curlook et al. | |
| 3,793,005 A | 2/1974 | Kelly et al. | |
| 4,317,748 A * | 3/1982 | Torok | B01J 37/20 502/337 |
| 5,478,791 A * | 12/1995 | Baldauf | B01J 23/755 502/337 |
| 6,677,271 B1 * | 1/2004 | Birke | B01J 35/0013 502/337 |
| 6,680,280 B1 * | 1/2004 | Birke | B01J 35/0073 502/337 |
| 8,969,606 B2 * | 3/2015 | Medhekar | B01J 31/22 556/13 |
| 10,537,885 B2 * | 1/2020 | Medhekar | B01J 35/1009 |
| 2003/0103893 A1 * | 6/2003 | de Lasa | C01B 3/40 423/653 |
| 2006/0107792 A1 | 5/2006 | Collins et al. | |
| 2011/0201847 A1 * | 8/2011 | Wolk | B01J 35/023 568/813 |
| 2013/0143730 A1 | 6/2013 | Fraga-Dubreuil et al. | |
| 2013/0144079 A1 | 6/2013 | Medhekar et al. | |
| 2013/0144082 A1 | 6/2013 | Fraga-Dubreuil et al. | |
| 2015/0196900 A1 | 7/2015 | Fraga-Dubreuil et al. | |

FOREIGN PATENT DOCUMENTS

| | | |
|---|---|---|
| TW | 201609251 A | 3/2016 |
| WO | 02/07880 A1 | 1/2002 |
| WO | 2011/075494 A1 | 6/2011 |
| WO | 2011/075496 A1 | 6/2011 |
| WO | 2016/004219 A1 | 1/2016 |
| WO | 2017/184710 A1 | 10/2017 |

OTHER PUBLICATIONS

Wikipedia, "Raney Nickel", May 3, 2015, 7 pages.
Compo et al., "Minimum Sintering Temperatures and Defluidization Characteristics of Fluidizable Particles", Powder Technology, vol. 51, Issue 1, 1987, pp. 85-101.
Crosa et al., "Determination of Mean Crystallite Dimensions from X-Ray Diffraction Peak Profiles: A Comparative Analysis of Synthetic Hematites", Clays and Clay Materials, vol. 47, No. 6, 1999, pp. 742-747.
Panigrahi et al., "Dilatometry of Ball Milled Nickel Nano Powder During Non-Isothermal Sintering", Science of Sintering, vol. 39, Issue 1, 2007, pp. 25-29.
Ramdhani et al., "Advances in Research on Nickel Production Through the Caron Process", Proceedings of EMC, 2009, pp. 899-913.
Huo et. al., "Recent Status and Prospect of Nano-Nickel Based Hydrogenation Catalyst", Powder Metallurgy Industry, vol. 16, No. 1, Feb. 28, 2006, pp. 45-48 (Abstract enclosed).
"Section III, Nickel Catalyst", "Catalyst Handbook", edited by Kei Miyazaki, Chemical Industry Press, Apr. 30, 1982, pp. 597-617 (Abstract enclosed).

* cited by examiner

HETEROGENEOUS CATALYST PROCESS AND NICKEL CATALYST

BACKGROUND

U.S. Pat. No. 1,628,190 to Raney discloses high surface-area sponge nickel, also known in the industry as sponge-nickel catalyst. Various grades of high surface area sponge nickel catalysts are marketed under the tradename "Raney®" nickel by W. R. Grace of Columbia, Md. Sponge nickel catalysts are often prepared by dissolving nickel in molten aluminum and then leaching away the aluminum with strong aqueous base such as NaOH. Other metals can be added at various points during production to tailor the catalytic activity of the finished catalyst for a particular end use.

In the case of sponge nickel as taught in the '190 Raney patent, it is difficult to obtain a sponge nickel catalyst essentially free of aluminum and sodium when the starting material is liquid aluminum and the extraction solvent is aqueous sodium hydroxide.

Reduction of nickel is described in several references, such as U.S. Pat. Nos. 3,793,005, 3,656,934, 2,000,171 and Rhamdhani et al., Proc. Eur. Metal. Conf. pp. 899-913 (2009). However, such processes do not provide optimal nickel metal particles for making nickel catalysts due to impurities, particle agglomeration, high temperatures employed during reduction, and other factors.

Finely divided nickel particles can also be desirable, especially for fluid bed operations. But processing finely divided nickel source material towards producing active nickel is a difficult process because such fine particles are often cohesive. Further, the nickel particles can sinter at temperatures as low as 200° C. (P. Compo et.al., Powder Technology, 51: 85-101 (1987); B. B. Panigrahi et.al., Science of Sintering, 39: 25-29 (2007)). Production of active nickel in a fluidized bed reactor requires additional steps and careful monitoring to minimize this sintering and agglomeration phenomena due to cohesive forces of attraction between particles. This has previously been accomplished by adding some amount of steam to the process (see, earlier filed U.S. Patent No. 20130144079) and by adjusting other variables. However, there are several limitations to the fluidized bed/steam processing technique that undermine its utility, such as the low amounts of hydrogen that can be utilized when steam is present, and the quality of nickel produced due to presence of steam.

SUMMARY

The present disclosure describes hydrogenation catalysts that can be produced by reducing nickel(II) to form relatively high surface area nickel at high purity. Further disclosed are high surface area nickel metals that can be substantially free from one or more of aluminum and sodium.

In various embodiments, the present invention provides a method of making a hetergeneous catalyst including particulate nickel metal (Ni(0)). The method includes calcining first nickel(II)-containing particles in an atmosphere including oxidizing constituents to generate second nickel(II)-containing particles. The method includes reducing the second nickel(II)-containing particles in a reducing atmosphere while rotating or turning the second nickel(II)-containing particles at about 275° C. to about 360° C. for a time sufficient to generate the particulate nickel metal (Ni(0)), wherein the particulate nickel metal (Ni(0)) is free flowing.

In various embodiments, the present invention provides a heterogeneous catalyst including particulate nickel metal (Ni(0)) formed by a method including calcining first nickel (II)-containing particles in an atmosphere including oxidizing constituents to generate second nickel(II)-containing particles. The method also includes reducing the second nickel(II)-containing particles in a reducing atmosphere while rotating or turning the second nickel(II)-containing particles at about 275° C. to about 360° C. for a time sufficient to generate the particulate nickel metal (Ni(0)), wherein the particulate nickel metal (Ni(0)) is free-flowing.

In various embodiments, the present invention provides a heterogeneous catalyst including particulate nickel metal (Ni(0)). The heterogeneous catalyst includes a hydrogen-reduced nickel(II)-containing particle.

In various embodiments, the present invention provides a heterogeneous catalyst including particulate nickel metal (Ni(0)). The heterogeneous catalyst has a BET Specific Surface Area of at least about 1 $m^2/g$. At least 10% of the particles of the heterogeneous catalyst having particle size (D10) of no greater than about 6 μm. The heterogeneous catalyst has an aluminum content less than about 1 wt %.

In various embodiments, the present invention provides a heterogeneous catalyst including particulate nickel metal (Ni(0)), the heterogeneous catalyst including nickel crystallites, The heterogeneous catalyst has a BET Specific Surface Area of at least about 1 $m^2/g$. At least 10% of the nickel crystallites have a size (C10) that is less than about 20 nm. The nickel crystallites have an average crystallite size of no greater than about 100 nm. The nickel crystallite size distribution span is greater than about 1.0.

In various embodiments, the present invention provides a method of heterogeneous including contacting a starting material with an embodiment of the heterogeneous catalyst including particulate nickel metal (Ni(0)) disclosed herein under conditions sufficient to hydrogenate the starting material.

In various embodiments, the present invention has certain advantages as compared to other heterogeneous catalysts, methods of making the same, and methods of using the same, at least some of which are unexpected. Disclosed are heterogeneous catalysts including nickel metal (Ni(0)) which can be made in a rotary processor. The catalysts can be free-flowing nickel metal powder made without addition of water or steam. In various embodiments, the methods can utilize higher concentrations of reductant, operate more quickly, and produce nickel metal with improved reactivity, such as compared to that produced by methods that rely upon fluidized bed reactors and the use of steam. The nickel metal powder as described herein can be free-flowing, which not only makes handling easier but improves the reactivity of the material.

In contrast to other nickel catalysts such as sponge-nickel catalyst, the disclosed heterogeneous catalyst does not require extraction of alumina using high-pH solutions such as aqueous NaOH or KOH. Thus, in various embodiments, the heterogeneous catalyst of the present invention can have substantially no impurities, such as aluminum, sodium, potassium, or a combination thereof. In various embodiments, the heterogeneous catalyst of the present invention can have less impurities, such as aluminum, sodium, potassium, or a combination thereof, as compared to other nickel catalysts such as sponge-nickel catalyst. In various embodiments, a hydrogenation catalyst comprising the disclosed heterogeneous catalyst can have greater hydrogenation activity (e.g., hydrogenates at a higher rate) as compared to other heterogeneous catalysts used under the same conditions such as sponge-nickel catalyst. In various embodiments, the heterogeneous catalyst of the present invention can be a closely controlled composition with relatively small physical dimensions and high surface area.

In various embodiments, the heterogeneous catalyst of the present invention can be produced with less or no use of nickel-aluminum alloys, as compared to other nickel catalysts such as sponge-nickel catalyst. In various embodiments, the heterogeneous catalyst of the present invention can be produced with less or no caustic extraction, as compared to other nickel catalysts such as sponge-nickel catalyst.

BRIEF DESCRIPTION OF THE FIGURES

The drawings illustrate generally, by way of example, but not by way of limitation, various embodiments

DETAILED DESCRIPTION

Figure 1:
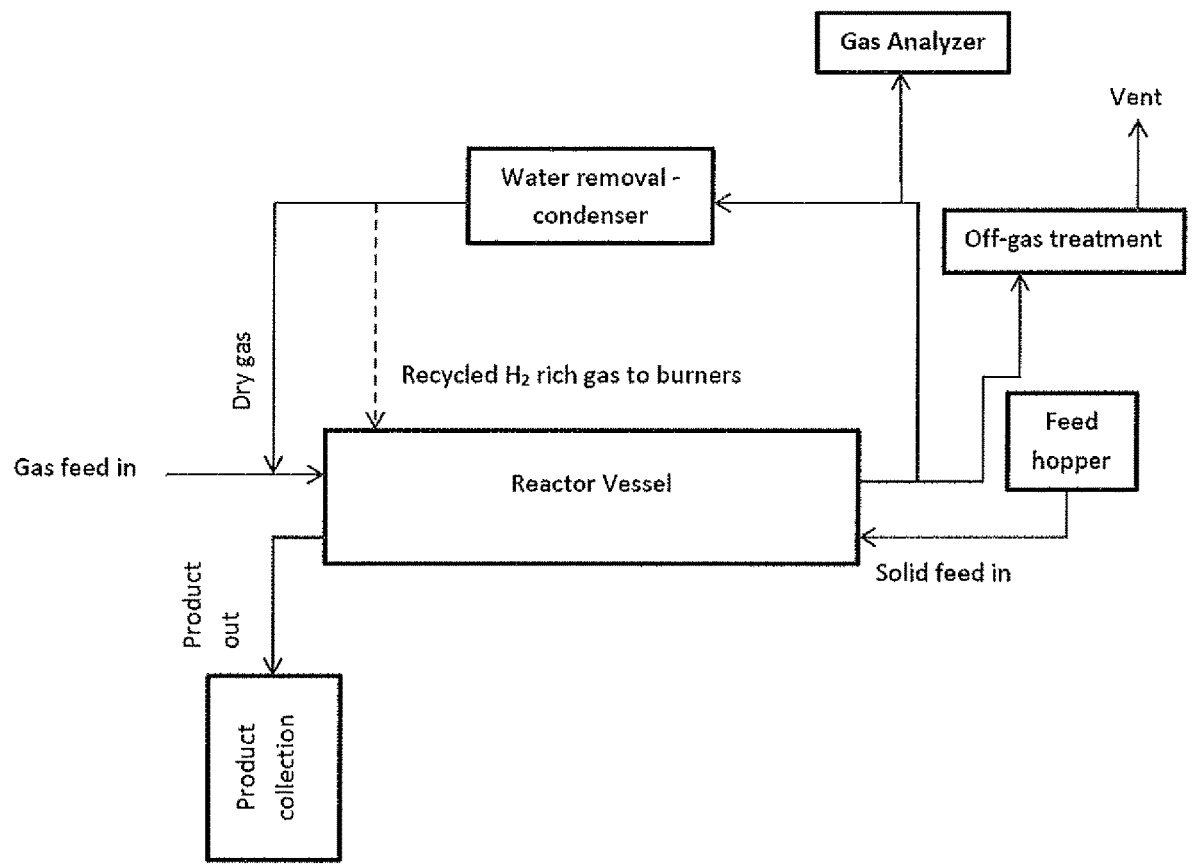
FIG. 1 illustrates a method for forming Ni(0) powder, in accordance with various embodiments.

As used herein, "agglomeration" or "to agglomerate" means that particles adhere to one another. The cohesive forces between agglomerated particles can be such that particles cannot be readily separated from the agglomerates. In some instances, agglomerated particles are sintered together. Friable agglomerated particles are not sintered together and can crumble apart to form usable particles, for example, when the friable agglomerates are gently tumbled, or gently crushed.

BET surface area, or gas absorption, measurement techniques can be used to measure the surface area and porosity of the particles present in a sample. Molecules of an adsorbate gas are physically adsorbed onto the particle surfaces, including the surfaces of any pores or crystallites, under controlled conditions within a vacuum chamber. For example, BET Specific Surface Area (BET SSA) can be measured by observing nitrogen adsorption using the Tristar 3000 Nitrogen Adsorption Instrument after degassing the samples under vacuum overnight at 105° C. to 200° C. Multi-point BET measurements can be made using a partial pressure range of 0.05-0.3 $P/P_0$. An adsorption isotherm can be obtained by measuring the pressure of the gas above the sample as a function of the volume of gas introduced into the chamber. The linear region of the adsorption isotherm can then be used to determine the volume of gas required to form a monolayer across the available particle surface area, using BET theory, as described by the following equation:

$$\frac{1}{v[(P/P_0)-1]} = \frac{c-1}{v_m}\left(\frac{P}{P_0}\right) + \frac{1}{v_m c}$$

where $v$ is the volume of gas, P is the pressure, $P_0$ is the saturation pressure, $v_m$ is the volume of gas required to form a monolayer and c is the BET constant. Plotting relative pressure, $\varphi$ (=$P/P_0$), and volume allows the volume of a monolayer to be determined from the gradient and intercept of the line.

The ratio BET SSA/C50 provides a value that is independent of the crystallite's geometry. The values obtained for a set of samples, can be correlated with "nickel activity" as defined here, and a reasonable linear correlation between activity and BET SSA/C50 has been found, as discussed herein.

Laser Diffraction Specific Surface Area (LD SSA) and particle size distribution (PSD) can be measured with a Mastersizer 2000 Particle Size Analyser (e.g., from Malvern Instruments Ltd using the Hydro 2000MU accessory and water as the dispersant). Light having a certain wavelength measured in micrometers is diffracted by the smaller size particles. The angle of diffraction will depend on the range of sizes present. The following equation can be used to report the Specific Surface Area (SSA):

$$SSA = \frac{6\sum \frac{V_i}{d_i}}{\rho \sum V_i} = \frac{6}{\rho D[3,2]}$$

where $V_i$ is the relative volume in class i with a mean class diameter of $d_i$, $\rho$ is the density of the material, and $D[3,2]$ is the surface area weighted mean diameter. This calculation can be carried out automatically within the laser diffraction system software. LD SSA provides a means of rapidly estimating the particle surface area. In carrying out this calculation, it is often assumed that the particles are substantially spherical, solid spheres.

A "crystallite" is a region within a particle of local crystalline order. Each active nickel metal (Ni(0)) particle comprises a large number of crystallites.

The term "crystallite size" as used herein refers to an average diameter for a possibly irregularly-shaped crystallite. Crystallite size can be measured as a diameter of the crystallite, for example, along the crystallite's major dimension, or as the cube root of the volume of the crystallite. The crystallite size can be determined by x-ray diffraction (XRD) analysis using procedures and equipment available in the art. An "average crystallite size" or "mean crystallite size" refers to an average (mean) value for a population of crystallite sizes as defined above. An average crystallite size can also be defined as the cube root of the average volume of a sample comprising multiple crystallites, and assumes that all crystallites have the same size and shape. For a distribution of sizes, the mean size can be defined as the mean value of the cube roots of the individual crystallite volumes or the cube root of the mean value of the volumes of the individual crystallites.

The term "C10" is a measure of crystallite sizes in the nickel metal (Ni(0)) particles, and refers to the largest diameter (e.g., in nanometers) that the smallest 10% of crystallites have in the nickel metal (Ni(0)) particles. The term "C50" is also a measure of crystallite sizes in the nickel metal (Ni(0)) particles, and refers to a diameter (size) wherein 50% of the Ni crystallites in a bulk sample have a size less than the stated value. The C50 value is also referred to herein as the mean crystallite size (MCS). The term "C90" is also a measure of crystallite sizes in the nickel metal (Ni(0)) particles, and refers to a diameter (size) wherein 90% of the nickel crystallites in a bulk sample have a size less than the stated value. Cx is the size of the crystallite for which x % of the sample has a smaller size. Crystallite size can be measured using X-ray diffraction (XRD).

The term "crystallite size distribution span" as used herein refers to a statistical value denoting a spread in crystallite size defined as (C90-C10)/C50.

A "surface crystallite" as the term is used herein refers to a crystallite contained within a particle, but wherein a portion of the crystallite is exposed to the environment surrounding the particle. To calculate BET SSA/crystallite size ratios, the equations BET SSA/$4\pi(C50/2)^2$ for spherical crystallites and BET SSA/$C50^2$ for cuboidal crystallites (cross section of cubes) can be used.

A surface crystallite "edge" as the term is used herein refers to those surface portions of a crystallite that are not planar surfaces.

Though the shape of crystallites is usually irregular, the shapes can often be described as being spherical, cuboidal, tetrahedral, octahedral, or parallelepipeds such as needles or plates, prisms or cylinders. Most applications of Scherrer analysis assume spherical crystallite shapes. If the average crystallite shape is known from another analysis, a proper value can be selected for the Scherrer constant K. Anistropic peak shapes can be identified by anistropic peak broadening if the dimensions of a crystallite are 2x*2y*200z, then (h00) and (0k0) peaks will be more broadened then (001) peaks. Also, see the discussion at this website: clays.org/journal/archive/volume %2047/47-6-742.pdf, published as M. Crosa, et al. (1999), "Determination of Mean Crystallite Dimensions from X-Ray Diffraction Peak Profiles: A Comparative Analysis of Synthetic Hematites", *Clays and Clay Materials,* 47(6), 742-747, and references contained therein, which reference and cited references are incorporated herein by reference in their entireties. The average number of crystallites per unit mass is expressed as the number of crystallites per gram of the nickel form, and any assumptions made about crystallite shape in carrying out the calculations are stated.

The term "D10" is a measure of particle sizes in the nickel metal (Ni(0)) particles, and refers to the largest diameter (e.g., in microns) that the smallest 10% of nickel metal (Ni(0)) particles have.

A "Ni particle" is a discrete particle or agglomerated particle, typically visible in a scanning electron micrograph.

The term "particle size" as used herein refers to an average diameter of a possibly irregularly-shaped particle. Such a particle size can be determined by measurement with a Mastersizer 2000 Particle Size Analyser from Malvern Instruments Ltd using the Hydro 2000MU accessory and water as the dispersant, as is well known in the art. An "average particle size" or "mean particle size" refers to an average (mean) value for a population of particle sizes as defined above. For sizes below 100-200 microns the average particle size can be measured using a laser diffraction technique.

"Substantially spherical" refers to particles or crystallites that are substantially symmetrical around a center point. For example, while the distance (radius) from a center point to the surface of a substantially spherical particle or crystallite can vary, such variation is not so great or so predictable that the shape of the substantially spherical particle or crystallite would more accurately be defined as another geometric shape (e.g., as a cube instead of as a sphere). In some embodiments, the substantially spherical particle or crystallite can have a radius that varies by about up to about 25%, or up to about 20%, or up to about 15%, or up to about 10%, or up to about 5%. In some embodiments, the substantially spherical particle or crystallite can be partially spherical. For example, the substantially spherical particle or crystallite can be hemispherical, or be a quarter of a sphere. The substantially spherical crystallite can be fused to a particle or another crystallite such that the substantially spherical crystallite is a partial, substantially spherical projection from the particle or other crystallite. A partially substantially spherical crystallite that is fused to a particle or another crystallite can therefore be about 25% to about 95% of a sphere, or any percentage of a sphere between 25% and 95%.

The Scherrer method (using full width at half maximum, FWHM, method) gives the ratio of the root-mean-fourth-power to the root-mean-square value of the thickness. The Stokes and Wilson method (using integral breadth) determines the volume average of the thickness of the crystallites measured perpendicular to the reflecting plane. The variance methods give the ratio of the total volume of the crystallites to the total area of their projection on a plane parallel to the reflecting planes.

All values shown as % or ppm (parts per million) are intended to be by weight, unless otherwise specifically stated (e.g., as volume %). In other words, a numerical percentage or a numerical parts per million is that numerical percentage or parts per million by weight of the total composition (unless otherwise specified).

First and Second Nickel(II)-Containing Particles.

Suitable second nickel(II)-containing particles from which the heterogeneous catalyst including particulate nickel metal (Ni(0)) can be prepared include, for example, those selected from any of basic nickel carbonate, nickel oxide, nickel carbonate, nickel bicarbonate, nickel oxalate, nickel formate, nickel squarate, nickel hydroxide, nickel oxide and combinations thereof. Other second nickel(II) particles include nickel nitrate, nickel cyanate and nickel sulfate. Many nickel(II)-containing particles are potentially useful.

The second nickel(II)-containing particles can be reduced directly into particulate nickel metal (Ni(0)) with a reductant (e.g., hydrogen) at moderate temperatures. Such a direct process is referred to as a one-step process. Alternatively, first nickel(II)-containing particles can first be subjected to calcination, which removes volatile components such as carbon dioxide and water, to form the second nickel(II)-containing particles, which can then be reduced within an atmosphere containing the reductant (e.g., hydrogen) at moderate temperatures.

The first nickel(II)-containing particles that are first subjected to calcination can include basic nickel carbonate, nickel oxide, nickel carbonate, nickel bicarbonate, nickel oxalate, nickel formate, nickel squarate, nickel hydroxide, nickel nitrate, nickel cyanate, nickel sulfate and combinations thereof. Calcination of the first nickel(II)-containing particles can generate the second nickel(II)-containing particles. When calcination is performed before reduction, the process is called a two-step process.

Nickel(II) particles that evolve carbon dioxide in a calcination step are useful as first nickel(II)-containing particles for making nickel metal. The first nickel(II)-containing particles that include substantial amounts of basic nickel carbonate, nickel hydroxide, nickel carbonate, and/or nickel oxide are especially useful. As used herein, basic nickel carbonate includes inorganic compounds such as nickel and carbonate. For example, basic nickel carbonate can be $Ni_4CO_3(OH)_6 \cdot 4H_2O$ or it can include simpler carbonates such as NiCO$_3$ and its hydrate (for example, NiCO$_3$.4H$_2$O, NiCO$_3$.6H$_2$O, and the like. Basic nickel carbonate can be described with the following chemical formula:

wherein x=z−y/2; y=2 z−2 x; z=1 to 100; and n=0 to 400.

Basic nickel carbonate (BNC) can therefore be employed as, or can be included within, the second nickel(II)-containing particles processed to generate nickel metal.

Basic nickel carbonate is available commercially. Different sources of nickel(II) particles can have different compositions. For example, basic nickel carbonate can be obtained from MetChem Corporation, an American distributor of this material. According to the vendor, the MetChem basic nickel carbonate is produced by precipitating the basic nickel carbonate from an aqueous solution including nickel, ammonia, ammonium carbonate, and water. The nickel is from an ore including nickel. Hence, the MetChem basic nickel carbonate can include at least one element selected from the group consisting of aluminum, calcium, cobalt, copper, iron, magnesium, manganese, sodium, sulfur, and zinc. One sample of MetChem basic nickel carbonate had a chemical analysis shown in Table 1.

TABLE 1

Analysis of MetChem Basic Nickel Carbonate Powder.
Nickel 47% by weight

| Cobalt 65 ppm | Copper 20 ppm | Iron 55 ppm | Zinc 12 ppm |
|---|---|---|---|
| Magnesium 60 ppm | Calcium 60 ppm | Sodium 60 ppm | Sulfur 175 ppm |

Different sources of nickel(II)-containing particles can have different contaminants as illustrated in Table 1 above. For example, the nickel(II)-containing particles can have less than 10 wt % impurities, 7, 5, 4, 3, 2, 1, 0.7, 0.6, 0.5, 0.4, 0.3, 0.2, 0.1, 0.07, 0.05, 0.03, or less than 0.01 wt % impurities.

For example, the first or second nickel(II)-containing particles employed in the methods described herein can have less than 100 ppm cobalt, less than 100 ppm copper, less than 100 ppm iron, less than 100 ppm zinc, less than 100 ppm magnesium, less than 100 ppm calcium, and less than 100 ppm sodium. In some instances, the first or second nickel(II)-containing particles employed in the methods described herein have less than 75 ppm cobalt, less than 30 ppm copper, less than 75 ppm iron, less than 30 ppm zinc, less than 75 ppm magnesium, less than 750 ppm calcium, and less than 75 ppm sodium.

Different commercial sources or batches of nickel(II)-containing materials can also include different amounts of water and/or carbon dioxide. Some types of nickel(II)-containing materials release the carbon dioxide more readily during calcination than others. If residual carbon dioxide remains in the nickel(II)-containing particles the reduction step may not generate an optimal nickel(II)-containing particles product or an optimal nickel metal (Ni(0)) product. In general, nickel(II)-containing materials that release significant amounts of carbon dioxide during reduction produce poorly reactive nickel metal. Hence, calcination is carried out at a temperature sufficient to release carbon dioxide, and the calcination proceeds until carbon dioxide is no longer released from the nickel(II) particles. Upon reduction, the nickel metal (Ni(0)) product has improved reactivity.

Basic nickel carbonate is a useful source of nickel(II)-containing particles. However, it may be desirable to manufacture the basic nickel carbonate rather than obtaining it from a commercial source to avoid impurities and inconsistencies in processing. The composition of the basic nickel carbonate can be controlled by manufacture of the basic nickel carbonate using selected reactants and manufacturing conditions.

Suitable basic nickel carbonates can be produced by precipitating the basic nickel(II) carbonate from an aqueous solution including nickel(II), carbonate anion, and water. For example, basic nickel carbonate can be produced by precipitating it from at least one aqueous solution selected from the group consisting of (1) an aqueous solution including nickel(II), ammonia, ammonium carbonate, and water; (2) an aqueous solution including nickel(II), carbonate anions, and water; and (3) an aqueous solution including nickel(II), bicarbonate anions, and water.

Basic nickel carbonate compositions can be made by adding a precipitant solution to a nickel solution in a precipitation reactor to form a reaction mixture and precipitating a nickel composition from the reaction mixture, wherein the nickel solution includes nickel(II) ions and water. The precipitant solution can be selected from the group consisting of: (a) bicarbonate ions and water, (b) carbonate ions and water, and (c) mixtures thereof. The mole ratio of bicarbonate ions to nickel ions in the reaction mixture after adding the precipitant solution can range from 0.1:1 to 2:1. Blends of bicarbonates and carbonates can also be used in the precipitant solution. Further information on preparing and using basic nickel carbonate is available in PCT/US2010/060388, filed Dec. 15, 2010 and published as WO/2011/075496, and in PCT/US2010/060381, also filed on Dec. 15, 2010 and published as WO/2011/075494, which are both specifically incorporated herein by reference in their entireties. A highly pure basic nickel carbonate with predictable and substantially uniform calcination and reduction properties can therefore be produced.

Calcination and reduction can be carried out in the same reactor. Previously, it was thought that the reactor should provide substantially uniform conditions for calcination and reduction such that the temperature is substantially uniform throughout the reactor, the atmosphere (e.g., reductant) is dispersed throughout the reactor and the nickel(II) particles are uniformly exposed to the atmosphere. However, such uniformity is not necessarily desirable. Gently turning of second nickel(II) particles so that the particles on the surface of the particle bed contact fresh reductant while particles within the body of the particle bed are later contacted with reductant can surprisingly provide improved product. Such gentle mixing avoids hot spots of exothermic reduction throughout the particle bed, which minimizes particle sintering. Gentle mixing reactors such as a rotary processor provide such conditions. Calcination and reduction of the nickel(II) particles can be performed in the same gentle-mixing reactor. Based on the objective of producing free flowing nickel metal (Ni(0)) particles, reduction in such a gentle-mixing reactor can be more effective than in other reactors such as fluidized bed reactors. Thus, the methods described herein are advantageously performed in a gentle-mixing reactor (e.g., rotary processor).

An embodiment of the method for forming the nickel metal (Ni(0)) powder is illustrated in FIG. 1. The gas phase (e.g., atmosphere including oxidizing constituents or reducing atmosphere) can flow in a counter-current fashion over or through the nickel solid phase (e.g., the first or second nickel(II)-containing particles). Such a counter-current flow mode means the two or more reacting phases are traveling in the opposite direction of each other. In other embodiments, the contact between the two phases can occur in a co-current flow mode. The co-current flow mode means the two or more reacting phases are travelling in the same direction of each other. Other flow modes for the contact may include, but not limited to, sparged-flow, cross-flow, up-flow, down-flow, laminar-flow, turbulent-flow, thin film-flow, dispersion-flow, circulatory-flow, and combinations thereof.

The first nickel(II)-containing particles can be charged into or placed within a rotary reactor, which rotates the particles to contact the nickel(II) with an atmosphere that flows through the processor. For calcination, the atmosphere that flows through the processor can be a gas containing one or more oxidizing constituent(s), optionally in an inert carrier gas. For example, the calcination atmosphere can include air, oxygen, ozone, or combinations thereof in a carrier such as nitrogen, argon, helium, or combinations thereof. Air is an inexpensive and effective calcination atmosphere. Calcination of the first nickel(II)-containing particles generates second nickel(II)-containing particles that have volatile components removed. The second nickel(II)-containing particles can then be reduced to nickel metal (Ni(0)). During reduction the atmosphere contains a reductant such as hydrogen, methane, higher carbon hydrocarbons, ammonia, synthetic gas ($H_2/CO$) or a mixture thereof.

In one embodiment, the spent calcination off-gas may be treated by such common industrial practices as cyclone separation, condensation drying, membrane separation, absorption scrubbing (e.g. for $CO_2$), and circulated back into the process with fresh make-up gas added as needed. In another embodiment, the chemically released water during the calcination process may be condensed from the spent off-gas, collected and re-used for non-process applications, while the dry gas containing a majority of oxidizing constituents in an inert carrier (e.g. $O_2$ in $N_2$) may be circulated back into the process.

In some embodiments, the gas feeds of desired quality may be obtained from other processes such as from chemical reactions, petro-chemical refining, combustion, scrubbing, bio-refining, fuel-cell operations, water electrolysis, gas separation, or combinations thereof. In other embodiments, the gas feeds of desired quality may be supplied by industrial gas producers.

Addition of Sulfur.

The method of forming the heterogeneous catalyst including particulate nickel metal (Ni(0)) can include adding sulfur (e.g., a sulfur source) to the first nickel(II)-containing particles, the second nickel(II)-containing particles, or a combination thereof. The sulfur source can be added to a nickel(II)-containing particle during manufacture of the nickel(II)-containing metal particles, of the sulfur source can be added to the nickel(II)-containing particle itself.

The nickel(II)-containing particle, or a starting material therefor, can be in solution, in suspension, or in particulate form during treatment with a sulfur source. For example, the nickel can be in particulate form within a liquid medium or within a gas stream. The solubility of nickel metal (Ni(0)) is generally quite low in many liquid solvents, but it can be suspended in a liquid or by a gas. Alternatively, the solid first or second nickel(II)-containing particles can simply be mixed with the sulfur source.

The sulfur source can be combined or mixed with the nickel(II)-containing particle, or a starting material therefor, for varying times. For example, the nickel(II)-containing particle, or a starting material therefor, and a sulfur source can be mixed together for about 1 minute to about 72 hours, or about 1 minute to 24 hours, or about 1 minute to 12 hours, or about 1 minute to 4 hours, or about 1 minute to 2 hours, or about 1 minute to 1 hour. Little mixing may initially be needed when the sulfur source is added to a nickel(II)-containing particle, or a starting material therefor, that is subjected to further processes involving mixing, such as calcination, reduction or even catalyst complex formation.

During treatment of nickel(II)-containing particle or a starting material therefor, the sulfur source-containing mixture can be maintained at about 4° C. to about 450° C. Little or no additional heating or incubation may be needed to treat nickel(II)-containing particle or starting materials with a sulfur source because various steps in the formation of the nickel metal (Ni(0)) provide sufficient heating and mixing for the sulfur treatment. Thus, sulfur sources can be added to essentially any convenient step involved in the preparation of the nickel(II)-containing particles or the nickel metal (Ni(0)) particles.

Examples of suitable sulfur sources are those selected from the group consisting of elemental sulfur, sulfur-containing gases, sulfur-containing salts, sulfur-containing ions and combinations thereof. Additional examples of sulfur sources include those selected from the group consisting of hydrogen sulfide, nickel sulfate, nickel sulfite, nickel sulfide, nickel hyposulfite, nickel thiosulfate, sulfur trioxide, sulfur dioxide, sulfur monoxide, disulfur dichloride, sulfur dichloride, sulfur tetrachloride, sulfur chloride pentafluoride, disulfur decafluoride, sulfur hexafluoride, sulfur tetrafluoride, sulfur trifluoride, and combinations thereof. The sulfur source can be 95 wt % to 99.9 wt %, or 99.99 wt %, or 99.999 wt % or more, free of silicon, sodium, potassium, calcium, magnesium, phosphorus, aluminium, copper, tungsten, mercury, iron, and combinations thereof. The sulfur source can be elemental sulfur.

Elemental sulfur can be present in a number of forms, including solid elemental sulfur, gaseous sulfur, polymeric sulfur, mixtures of polymeric chains of sulfur, cyclic sulfur and combinations thereof. There are also a large number of allotropes of sulfur. The most common form found in nature is yellow orthorhombic α-sulfur, which contains puckered rings of eight sulfur atoms ($S_8$). In addition, other solid forms of sulfur contain sulfur rings of 6, 7, 9-15, 18 and 20 atoms. There are also sulfur gases, such as $S_2$, $S_3$, $S_4$, and $S_5$. Metallic-like sulfur forms can also be formed, for example, at high-pressures. Any and all of these forms of sulfur are sulfur sources for use in the methods described herein.

The sulfur source can be added to the first or second nickel(II)-containing particles or a starting material therefor, such that, at the time of the calcining, the first or second nickel(II)-containing particles are about 0.001 wt % to about 10 wt % sulfur, on a nickel basis, or about 0.01 wt % to about 3 wt %, or 10 wt % or less, or less than, equal to, or greater than about 9 wt %, 8, 7, 6, 5, 4, 3, 2.5, 2, 1.5, 1.4, 1.3, 1.2, 1.1, 1, 0.9, 0.8, 0.7, 0.6, 0.5, 0.4, 0.3, 0.2, 0.1, 0.01, or about 0.001 wt % or less.

Reduction.

Reduction of the second nickel(II)-containing particles involves addition of electrons to nickel and a decrease in oxidation state of the nickel(II). Reduction is performed under conditions sufficient to reduce at least a portion of second nickel(II)-containing particles to particulate nickel metal, which can include an elevated temperature, an amount of reductant or a reducing agent, and a time sufficient to substantially reduce the nickel(II)-containing particles to form a particulate nickel metal (Ni(0)) powder. The nickel metal (Ni(0)) product is a particulate solid material that includes nickel metal (Ni(0)) in the form of a free-flowing powder.

A reductant can be used for such reduction. The reductant can be any gaseous or particulate substance that can reduce nickel(II) to nickel metal (Ni(0)). Examples of reductants include, for example, hydrogen, ammonia, carbon or carbon-containing compounds (such as coal or coke, methane, higher carbon hydrocarbons), and combinations thereof. The atmosphere can contain a reductant in an amount sufficient to reduce at least a portion of the nickel in the nickel(II)-containing particles to particulate nickel metal (Ni(0)). In some embodiments, the reductant does not include carbon-containing substances.

Hydrogen is a convenient and inexpensive reductant that is generally highly effective as a reductant. Moreover, when hydrogen is used as the reductant, the off-gas from the reduction process can contain significant amounts of hydrogen (e.g., 20% to 70% by volume) that can be recycled either back into the reduction process or to gas burners for heating the calcination and/or reduction vessel.

A carrier gas can be mixed with the reductant. For example, the carrier gas can be an oxygen-free gas such as a noble gas or nitrogen. Noble gases that can be employed include helium, neon, argon, krypton, or xenon. Deoxygenated air is another example of a substantially oxygen-free gas. Nitrogen is a convenient and fairly inexpensive carrier gas.

The percentage of reductant in the atmosphere of the reactor can be about 0.1% to 100% by volume, 5% to 85%, 50% to 85%, 55% to 80%, 60% to 75%, 65% to 75%, or about 70% by volume. One example of an effective atmosphere for a reduction gas includes about 70 vol % hydrogen, and about 30 vol % nitrogen.

Some previously available calcination and/or reduction methods have added steam to the reductant used in a batch or a fluidized bed system to prevent agglomeration of nickel particles during such processes. However, the concentration of hydrogen reductant that can be used in a fluidized bed system must be less than about 20% (vol/vol) hydrogen, or agglomeration will occur even when steam is added.

However, no such addition of steam or water is needed for reduction by the methods described herein. Nor is addition of water or steam to the gaseous atmosphere for reduction desirable when the methods described herein are employed. When the second nickel(II) particles to be reduced include nickel oxide, a hydrogen reduction process produces some steam (or water vapor) because the hydrogen chemically combines with the oxygen contained in the nickel oxide to generate water vapor as reduction proceeds. However, such an amount of steam generated during the nickel reduction process in a fluidized bed environment is not sufficient to prevent agglomeration. Instead, nickel(II) reduction in the fluidized bed environment must be supplemented with at least 10% or 20% steam, externally added to the reduction gas, to prevent particle agglomeration. In contrast, in embodiments of the present invention, nickel oxide is readily reduced by gentle mixing (e.g., in a rotary bed) to produce a free flowing product without any addition of water or steam to the reductant.

Added steam is not needed, and is not desirable, when the nickel(II) particles are reduced by gentle mixing (e.g., in a rotary processor). From extensive lab and gas fluidized solid bed testing, the inventors have identified that sintering of nickel particles is exacerbated by the higher collision rate among particles in a fluidized bed system when the particles are exposed to reduction conditions. Nickel particles can begin to soften at temperatures as low as 200° C. (P. Compo et.al., Powder Technology, 51: 85-101 (1987); B. B. Panigrahi et.al., Science of Sintering, 39: 25-29 (2007)). The inherent turbulence present in a fluidized bed system leads to more frequent and greater impact forces between particles. Such higher impact and more frequent particle collisions results in a greater exchange of energy between particles, which in turn results in greater propensity for particles to agglomerate. Such agglomeration can occur at temperatures as low as 300° C. The propensity for agglomeration is further increased by the exothermic reduction process. As the previous application U.S. Patent No. 20130144079 describes, addition of steam helps to minimize the agglomeration in a fluidized bed process. The presence of steam may also shift the equilibrium away from reduction because water is a product of the reduction process and when more water is present the reduction reaction equilibrium can shift away from reduction. Hence, although reduction fluidized bed provides the uniform thermal environment for the reduction, a greater propensity for agglomeration must be counter-balanced by the addition of steam to the process.

Although the use of steam at vol/vol percentages of 10% or more can reduce such agglomeration, the catalytic hydrogenation activity of nickel particles reduced in the presence of steam can be lower than when the nickel particles are reduced without steam. This can be due to sintering of nickel surfaces thereby reducing their specific surface area measured as BET surface area (0/g).

Fluidized bed reactors can lead to agglomeration of nickel particles, for example, because the particles undergo repeated high impact collisions while being heated to a point where some softening of the particles can occur. Such a process leads to sintering (agglomeration) of at least some of the particles. Some other types of reactors can lead to the same problems with agglomeration, such as systems where the nickel particles are significantly compressed against one another, such as a screw auger system, can lead to agglomeration of the particles.

When the collision impact velocity and compressive forces are minimized between particles a free-flowing reduced nickel product can be produced. There are several types of processors that can be employed to avoid nickel particle agglomeration. Examples include rotary type reactors, multiple hearth furnace reactors, and tubular packed reactors operated at close to atmospheric pressure (minimizing compressive forces). Systems that employ spray-dryer type equipment where the particles are highly dispersed in the gas phase to minimize particle-to-particle interaction can also be employed.

There are advantages to use of a rotary reactor for reduction. Up to 100 vol % hydrogen can be employed in the rotary processor, which is not possible in reactors where steam must be added (e.g., in fluidized bed reactors). The processing steps are simple and easier to control in the rotary processor than in other reactors. The consumables required for carrying out the processing in a rotary processor are also significantly lower than, for example, in a fluidized bed reactor. Most of the consumables used in the fluidized bed reactor process are utilized in keeping the bed fluidized. The processing of different raw materials in a fluidized bed system requires evaluating their individual fluidization characteristics, which can be costly, time consuming and not necessarily readily scalable. In comparison, in a rotary unit, there are no such issues in processing different supplier's raw material and as such is a much robust technology. Reduction in a rotary reactor is fast, energy efficient, and generates an improved product.

In the Examples described herein, fine second nickel(II)-containing particles (e.g., nickel oxide particles) are gently rolled inside a rotary kiln reactor with a co-current or counter-current flow of reducing gases. The reduction occurs at the exposed surface of the particles, which is continually refreshed as the kiln rotates. The reductive gases have to diffuse through the layers of solid particles, so the rate of reaction is limited by the rate of hydrogen diffusion. Thus, particles are not compressed or subjected to high impact forces, and fewer hot spots are present during the exothermic reduction process. The incidence of agglomeration is minimized.

Applicants have discovered that additional steam is therefore not needed when the nickel particles are not subject to high impact collisions or compression during reduction. Processors such as rotary processors prevent agglomeration and clumping of the reduced nickel product without the use of water vapor or steam, thereby facilitating removal of the product from the reaction vessel. When no steam is added to the rotary processor the reactivity of the nickel metal product is improved, for example, because the presence of steam reduces the particulate surface area of the nickel metal (Ni(0)) particles. Use of such equipment can improve the catalytic hydrogenation activity of the nickel metal (Ni(0)) particles.

A calcination step can be performed before reduction to remove residual water in first nickel(II) particles. Also prior to reduction, the reactor containing the nickel(II)-containing particles (e.g., the first nickel(II)-containing particles and/or the second nickel(II)-containing particles) can be flushed with a substantially oxygen-free gas to remove molecular oxygen and other undesired gases (e.g., carbon dioxide and any residual water vapor) from the apparatus and from the nickel(II)-containing particles. The reductant or reducing agent (e.g., hydrogen gas) can then be introduced into the atmosphere of the reactor so that a mixture of reducing agent and the substantially oxygen-free carrier flows through the reactor.

Gas flow rate during the process relates to the size and/or type of reactor equipment used for the reduction and is within the knowledge of the skilled person to select an appropriate rate. For example, in smaller reactors, the gas flow rate during reduction can be about 0.1-10 L/minute, or about 1-8 L/minute, or about 2-7 L/minute, or about 3-6 L/minute. In larger reactors a gas flow rate of about 5-80 L/minute, or about 10-70 L/minute, or about 15-60 L/minute, or about 20-50 L/minute, or about 25-40 L/minute, or about 25-35 L/minute. The gas flow rate can be adjusted as desired or it can be determined by the type of equipment used for the reduction.

Reactor pressure during the reduction step is not critical. Reduction can be performed at a pressure of about 0.1 atmospheres to 20 atmospheres, or at about 0.5 atmospheres to 10 atmospheres, or at about 0.5 atmospheres to 2 atmospheres. The reduction can conveniently be performed at about one atmosphere pressure.

The reduction step can be performed at a temperature between 150° C. and 800° C., for example, between 175° C. and 600° C., between 200° C. and 500° C., between 225° C. and 425° C., between 250° C. and 375° C., between 260° C. and 370° C., or between 270° C. and 365° C., or between 275° C. and 360° C., or between 280° C. and 355° C., or between 285° C. and 360° C., or between 290° C. and 360° C., or between 300° C. and 350° C. In some embodiments, the range of temperatures that can be employed includes any numerical range representing a temperature range falling between 250° C. and 375° C. Temperatures at the lower end of these ranges (e.g., 250° C.) can require longer reduction times. Reductions at high temperatures (e.g., 375° C. or higher) can, under some circumstances or conditions, yield agglomerated nickel, and/or nickel powders with lower hydrogenation activity.

The reduction time can be a function of the solids throughput, starting feed quality, pressure, temperature, gas-solid contacting efficiency and the flow rate and concentration of reducing gas. Reduction can typically be performed for about 0.5 hours to about 3 hours, or for about 0.75 hours to about 2.25 hours, or for about 0.9 hours to about 2.1 hours, or for about 1 to about 2 hours, when a stoichiometric excess of reductant is employed. For example, when temperatures between 300° C. and 350° C. are employed the reduction can be carried out 1-2 hours, provided a stoichiometric excess of reducing agent (e.g., hydrogen) is passed through the reactor to convert the nickel(II)-containing particles to nickel metal powder.

When hydrogen is used as the reducing agent, introduction of hydrogen to the reaction vessel can cause a temperature increase in the bed of nickel-containing particles, for example, of from about 10° C. to about 50° C., depending upon the concentration of hydrogen. One of skill in the art can readily adapt the conditions in the rotary reactor vessel to accommodate variations in temperature, reductant concentration and the like.

The reductant can be continuously added to the reduction vessel via an inlet valve and exit via an exit valve. Alternatively, a large excess of the reductant can be sealed with the nickel(II)-containing particles inside the reduction reactor. In general, the reductant can be continuously added to the reactor so that fresh reductant is continually available to the nickel particles.

The stoichiometric amount of hydrogen needed to reduce second nickel(II)-containing particles such as nickel oxide is theoretically a 1:1 molar ratio. The amount of reductant employed for reduction can be in excess of such a stoichiometric amount, in part because the contact efficiency of the reduction system employed can vary. For example, when hydrogen is used as the reducing agent in a rotary kiln reactor, the larger unoccupied volume of space inside the kiln provides an opportunity for some of the hydrogen to bypass the nickel particle bed. The amount of gas that bypasses the nickel particles is dependent on variety of factors that include the internal volume and shape of the reduction vessel, the rate of revolution or mixing, the solid feed rate, and the material burden volume. Hence, in practice the amount of hydrogen to nickel oxide needed is greater than a 1:1 molar ratio. For example, $H_2$/NiO molar ratios employed can be greater than 2:1. Examples of $H_2$/NiO molar ratios that can employed include ratios between about 1.9 and 2.5, or between about 2.0 to about 2.4. A molar ratio of $H_2$/NiO lower than 1.9, or between 1 and 2 can yield an under-reduced material even though sufficient hydrogen theoretically has been introduced, due to inefficient contact between the gas and particles during the reduction process. A person skilled in the art can readily improve this efficiency by changing the internal dimensions of the kiln, modulating the reductant gas flow rate, or increasing the residence time of the nickel oxide.

After reduction, the flow of hydrogen can be terminated. The rotary reactor can be flushed with substantially oxygen-free gas to remove residual hydrogen. The reduced nickel can be discharged to an oxygen-free vessel such as a tote. The tote can be purged with an oxygen-free gas, and/or have a fitting that allows purging with a selected gas, or evacuation of the gaseous atmosphere within the tote. The nickel metal (Ni(0))-containing product is stored in a vacuum or in a substantially oxygen-free gas. For example, the nickel metal produced by the reduction step can be stored under inert atmosphere, such as nitrogen or argon atmosphere, until use.

The amount of nickel metal generated and its purity can be determined by a metal analysis using methods known to the skilled person. Similarly, the amount of nickel in any of the nickel-containing compositions or particles used in the methods described herein can be determined by a metal analysis using methods known to the skilled person.

The nickel metal (Ni(0)) product generated nickel preparation can have less than 10 wt % impurities, or less than 7% impurities, or less than 5% impurities, or less than 4% impurities, or less than 3% impurities, or less than 2% impurities. In general, smaller percentages of impurities are desirable such as less than 1% impurities, or less than 0.7% impurities, or less than 0.6% impurities, or less than 0.5% impurities, or less than 0.4% impurities, or less than 0.3% impurities, or less than 0.2% impurities, or less than 0.1% impurities, or less than 0.07% impurities, or less than 0.05% impurities, or less than 0.03% impurities, or less than 0.01% impurities, or less than 0.005 wt % impurities. Examples of impurities can include aluminum, sodium, potassium, or any combination thereof.

The reductant from the reduction process can be recycled. For example, the spent reduction off-gas may be treated by commonly available industrial practices such as cyclone separation, condensation drying, membrane separation, and absorption scrubbing. Components of the off-gas can then be circulated back into the process, for example, with addition of fresh reductant and/or carrier gas. During reduction of some nickel(II)-containing materials water can be released. Usually, the water content of the reduction off-gas is only a few percent by volume. Such chemically released water process can be condensed out of the spent reduction off-gas. Water and other off-gas components can be collected and re-used for non-process applications, while the dry gas containing reductant with any remaining carrier gas (e.g. $H_2$ in $N_2$) can be circulated back into the process.

In some instances, it is more economical to utilize the off-gas, or components thereof, as fuel to heat the calcination or reduction vessel. For example, an externally fired natural gas heated rotary kiln can be adapted to burn hydrogen from the off-gas in addition to the natural gas. While the hydrogen in the off-gas from a reduction process can also be used for reduction of the nickel(II) particles as described above, the reduction process is generally more effective if highly pure, dry hydrogen is employed (e.g., with some pure dry carrier gas). The investment in recycle loop can be avoided if some of the hydrogen cost going in the off-gas can be recovered by using it as an energy source in the external gas fired burners. If electrical energy is used for heating the kiln, then purification of off-gas of steam and recycling the rest may be viable option.

Calcination.

Calcination can be used to remove volatile components from first nickel(II)-containing particles, to form the second nickel(II)-containing particles. The reduction is performed after the calcination.

Although first nickel(II)-containing particles can be reduced to nickel metal (Ni(0)) in one step, it may be useful to calcine the nickel-containing compositions prior to reduction. As used herein "calcine" or "calcining" or "calcination" is a thermal treatment process applied to nickel(II)-containing compositions in order to bring about a thermal decomposition, phase transition, or removal of a volatile fraction. Calcination can be performed using any available calcination procedure or apparatus in presence of appropriate gas environment such as air or nitrogen, or in other suitable media, or even in absence of gas environment such as partial or total vacuum.

In general, such a calcination step is carried out using conditions sufficient to calcine the nickel containing particles. The calcination can be performed under conditions sufficient to substantially remove volatile materials. Such volatile materials include carbon dioxide, nitrate, nitric acid, formate, formic acid, cyanate, hydrogen cyanide, sulfate, sulfuric acid, water and the like. For example, carbon dioxide or carbon dioxide and water can be the major volatile materials that are removed, particularly when the nickel(II)-containing composition is basic nickel carbonate. In some embodiments, the calcination can be performed under conditions sufficient to convert first nickel(II)-containing particles substantially into nickel(II) oxide (NiO).

Calcination can be carried out in any suitable reactor, such as a fluid bed reactor, a fixed bed reactor, an expanded fixed bed, a rotary kiln, a rotary pan, and other such equipment known to the skilled person. Calcination of nickel(II)-containing particles can conveniently be performed in a rotary processor, which can yield a nickel metal (Ni(0)) preparation that is highly reactive and free-flowing. Moreover, the produced nickel(II)-containing particles can be reduced in the same rotary processor as was used for calcination pursuant to the methods described herein.

The conditions within the rotary processor are adapted to calcine the nickel-containing particles. Generally, calcination can be carried out in any gas or atmosphere that does not react with nickel-containing salts or compound to form undesirable nickel-containing materials. The gas or atmosphere can contain oxygen. Suitable convenient gases for the calcination step include air and nitrogen; others can include argon and helium. Air is therefore conveniently used during many calcination procedures. Thus, conditions sufficient to calcine nickel-containing materials include contacting the first nickel(II)-containing particles with an atmosphere that contains oxygen (e.g., air).

Temperatures useful for calcination of first nickel(II)-containing particles include those in the range of about 250° C. to 600° C. Below 250° C. the calcination can be incomplete, so that the first nickel(II)-containing particles are not completely converted to second nickel(II)-containing particles. Instead, the partially calcined materials can contain volatile materials that can reduce the activity of the final nickel product. Above 600° C., excessive collapse or sintering of the first nickel(II)-containing particles may occur under some conditions, consequentially reducing the reactivity of the nickel powder product.

The time for optimal calcination varies inversely with the temperature: when lower temperatures are used (e.g., 250° C.) calcination can be performed for longer time periods (e.g., up to 18-20 hours). However, when calcination is performed at temperatures of about 300° C. to 600° C., a shorter time period is effective for calcination, for example, about 10 minutes to about 6 hours, or about 10 minutes to 4 hours. The time for the calcination step can range from tens of seconds at 600° C. to multiple hours at 250° C. In general, calcination of the first nickel(II)-containing composition is complete within about 30 minutes to 2 hours when using temperatures of about 350° C. to 500° C. Especially desirable calcinations temperatures are from about 400° C. to about 500° C. At temperatures between 450° C. and 500° C., calcination is substantially complete within about 1-2 hours.

Effective calcination can be monitored and detected by observing the release of volatile components such as carbon dioxide from the nickel(II)-containing composition and/or by observing the conversion of nickel(II)-containing salts and compounds within the composition to nickel oxide (and/or nickel hydroxide). Calcination can therefore continue until volatile materials (e.g. carbon dioxide and/or water) are no longer detected in the effluent gases emerging from the calcination chamber. In some cases, calcination can be continued for 5-60 minutes after volatile materials is no longer detected in the effluent gases emerging from the calcination chamber. For example, calcination can continue for 5-30 minutes, or for 5-20 minutes, or for 5-15 minutes after volatile materials are no longer detected in the effluent gases emerging from the calcination chamber.

After calcination is completed, the flow of oxygen-containing gas is terminated and the apparatus can be flushed with a non-oxygen-containing or inert gas. Nitrogen is useful for this purpose but other non-oxygen-containing or inert gases can also be used (e.g., noble gases such as argon or neon). The flow of the non-oxygen containing or inert gas is continued until oxygen is substantially removed from the reactor bed of the apparatus. The reduction of nickel in the calcination product can then be performed.

A rotary reactor can be employed to perform the steps of calcination and reduction of the nickel(II)-containing particles to nickel metal (Ni(0)) powder. Any available rotary reactor can be employed.

Hydrogenation Using the Heterogeneous Catalyst Including Particulate Nickel Metal (Ni(0)).

In various embodiments, the present invention provides a method of using the heterogeneous catalyst including particulate nickel metal (Ni(0)) described herein as a hydrogenation catalyst. For example, it can be used as a high purity high surface area alternative to sponge-nickel catalyst such as Raney® nickel.

In various embodiments, the present invention provides a method of hydrogenation. The method includes contacting a starting material with an embodiment of the hydrogenation catalyst including the particulate nickel metal (Ni(0)) described herein under conditions sufficient to hydrogenate the starting material. The hydrogenation of the starting material can include at least one of hydrogenation of an unsaturated compound, reductive alkylation of a carbonyl compound with an amine, hydrogenolysis of an ester or ether, dehydrogenation of a hydrocarbon or alcohol, dehalogenation, desulfurization, or a combination thereof. The hydrogenation of the starting material can include at least one of reduction of a nitro group to an amine group (e.g., converting a nitroaryl compound such as dinitrotoluene into an aminoaryl compound such as toluenediamine), reduction of a nitrile to an amine (e.g., converting stearonitrile to stearylamine, or adiponitrile to hexamethylenediamine), reduction of an aldehyde to an alcohol (e.g., converting dextrose to sorbitol), reduction of an olefin to a paraffin (e.g., converting sulfolene to sulfolane), reduction of an alkyne to a paraffin (e.g., converting 1,4-butynediol to 1,4-butanediol), and reduction of an aromatic compound to an aliphatic compound (e.g., converting benzene to cyclohexane, or converting phenol to cyclohexanol).

Other Properties of Nickel Metal (Ni(0)).

The properties described in this section can be properties of the nickel metal (Ni(0)) of any embodiment of the hydrogenation catalyst including nickel metal (Ni(0)) described herein.

U.S. Patent Publication No. 2013/0143730, entitled "Metal-Ligand Catalyst Formation," and U.S. Patent Publication No. 2013/0144082, entitled "Nickel Form for Preparation of Catalytic Nickel-Ligand Complexes," are hereby incorporated by reference in their entirety.

In various embodiments, the present invention provides a heterogeneous catalyst including particulate nickel metal (Ni(0)). The heterogeneous catalyst can have a BET Specific Surface Area of about 2 $m^2/g$ to about 200 $m^2/g$. At least 10% of the particles of the heterogeneous catalyst can have a particle size (D10) of no greater than about 6 μm. The heterogeneous catalyst can have an aluminum content less than about 1 wt % and a sodium content less than about 1 wt %.

In various embodiments, the present invention provides a heterogeneous catalyst including particulate nickel metal (Ni(0)), the heterogeneous catalyst including nickel crystallites. The heterogeneous catalyst has a BET Specific Surface Area of at least about 1 $m^2/g$. At least 10% of the nickel crystallites have a size (C10) that is less than about 20 nm. The nickel crystallites have an average crystallite size of no greater than about 100 nm. The nickel crystallite size distribution span is greater than about 1.0.

The nickel metal (Ni(0)) and heterogeneous catalyst including the same generated as described herein is a free-flowing powder that is highly reactive and pyrophoric upon exposure to oxygen (e.g., air). The average surface area, the porosity, and the distribution of surface areas of the nickel metal (Ni(0)) particles related to the ability of the material to perform as a heterogeneous catalyst.

As used herein, "free-flowing" as it relates to nickel metal (Ni(0)) particles means that the preparation contains particles of nickel that are so small that the preparation is substantially a powder. For example, desirable nickel metal (Ni(0)) particles include nickel particles with an average size that is no greater than about 150 nm, no greater than about 100 nm, no greater than about 70 nm, or no greater than about 50 nm. Although some agglomerates can form during the methods described herein, nickel metal (Ni(0)) particles can still be free-flowing so long as substantially all of the agglomerates are friable and readily break apart into small powdery particles. For example, nickel metal (Ni(0)) particles with agglomerates can become free-flowing nickel metal (Ni(0)) particles upon shaking or agitation of the preparation.

The methods described herein convert almost all of the first or second nickel(II)-containing particles to a free-flowing particulate nickel metal product. For example, the amounts of non-free-flowing nickel metal in the particulate nickel metal product generated as described herein is typically less than 7 wt %, or less than 6%, or less than 5%, or less than 4%, or less than 3.9%, or less than 3.8%, or less than 3.7%, or less than 3.6%, or less than 3.5 wt %. Other methods such as those involving use of steam in a fluidized bed can be less efficient and/or less reliable, often generating nickel product that has at least 7 wt %, or at least 8 wt % non-free-flowing in the final product. Methods that reproducibly generate less waste are desirable because they are less costly, more efficient, and reduce the need for waste disposal.

In general, a nickel metal (Ni(0)) particle with a higher BET SSA ($m^2$/gram) value is more active (performs as a hydrogenation catalyst) than a nickel metal (Ni(0)) particle with a lower BET SSA (m$^2$/gram) value. The particulate nickel metal products can have a BET SSA (m$^2$/gram) values of at least 2 m$^2$/gram, or of at least 4 m$^2$/gram, or of at least 5 m$^2$/gram. Nickel produced at a given temperature in presence of added steam typically result in lower BET SSA (m$^2$/gram) and contain higher amount of unconverted nickel (II)-containing particles when compared to nickel produced in absence of any added steam. The unconverted nickel(II)-containing particles in final nickel product is a waste product which is a cost penalty. Hence, the methods described herein in absence of additional steam are particularly useful because these methods can efficiently and reproducibly generate particulate nickel metal products with specific surface area measured as BET-SSA of at least about 2 m$^2$/g, at least about 4 m$^2$/g, or about 5 m$^2$/g to about 200 m$^2$/g, about 10 m$^2$/g to about 50 m$^2$/g, or less than or equal to about 2 m$^2$/g, or less than, equal to, or greater than about 3 m$^2$/g, 4, 5, 6, 7, 8, 9, 10, 11, 12, 14, 16, 18, 20, 25, 30, 35, 40, 45, 50, 55, 60, 70, 80, 90, 100, 120, 140, 160, 180 m$^2$/g, or about 200 m$^2$/g or more. In contrast, methods of generating nickel metal powders, for example in the presence of steam, are less efficient, less reliable, and produce a product that typically has less hydrogenation activity due to lower have BET SSA (m$^2$/gram) values (e.g., less than 9 m$^2$/gram, or less than 8 m$^2$/gram).

The surface area of nickel metal particulate preparations can also be measured by a Laser Diffraction Specific Surface Area technique. Nickel metal (Ni(0)) particles can have a Laser Diffraction Specific Surface Area of at least about 0.4 m$^2$/gm. Also, at least 10% of the nickel metal (Ni(0)) particles (D10) can have a diameter of no greater than about 4 μm. The nickel metal (Ni(0)) particles can have a ratio of BET Specific Surface Area to D10 of from 3 to 5 m$^2$/g/μm or about 0.5×10$^6$ m/g to about 5×10$^6$ m/g.

The surface characteristics of the nickel metal (Ni(0)) particles including the crystallites can be such that a ratio of BET Specific Surface Area to Laser Diffraction Specific Surface Area is about 15 to about 25, or about 20 to about 30. The nickel metal (Ni(0)) particles can have a BET Specific Surface Area/C50 ratio of not less than 0.07×10$^9$ m/g. The nickel metal (Ni(0)) particles can have a BET SSA/C50 ratio of at least about 0.1×10$^9$ m/g, or at least about 0.4×10$^9$ m/g. The nickel metal (Ni(0)) particles can have an LD SSA/C50 ratio of at least about 4.3×10$^6$, or at least about 10$^7$.

The nickel metal (Ni(0)) particles can have on average per gram at least about 10$^{15}$ surface crystallites per gram nickel, preferably at least about 5×10$^{15}$ surface crystallites per gram nickel, more preferably at least about 10$^{16}$ surface crystallites per gram nickel, even more preferably at least about 5×10$^{16}$ surface crystallites per gram nickel, and more preferably at least about 10$^{17}$ surface crystallites per gram nickel. The nickel metal (Ni(0)) particles can have on average at least about 10$^{16}$ surface crystallites per gram nickel that are smaller than or equal to size C10.

By a "surface crystallite" is meant a nickel crystallite on or within a nickel metal (Ni(0)) particle, where at least one side or edge of the crystallite is exposed to the surroundings. While not wishing to be bound by theory, the suitability of nickel metal (Ni(0)) particles having at least about 10$^{15}$ to 10$^{17}$ surface crystallites present is related to the presentation on the particle surface of numerous crystallite edges, which are believed to be more reactive than planar crystallite faces. The greater hydrogenation reactivity of the crystallite edges can be related to steric factors, electronic factors, or both in the interaction of the approaching starting material in solution to the surface of the nickel metal (Ni(0)) particles.

The desirable nickel metal (Ni(0)) particles can have nickel crystallites of average size of no greater than about 70 nm (e.g., instead of 100 nm) as determined by temperature programmed X-ray diffraction (TP-XRD); or preferably the nickel crystallites have an average crystallite size of no greater than about 50 nm (instead of 100 nm or 70 nm); or more preferably the nickel crystallites have an average crystallite size of no greater than about 30 nm (instead of 100 nm, 70 nm or 50 nm). In general, nickel metal (Ni(0)) particles with smaller nickel crystallites, particularly when combined with other desirable physical properties, are preferred. At least 10% of the nickel crystallites can have a size (C10) that is less than about 10 nm. The nickel crystallites can have an average crystallite size of no greater than about 20-25 nm.

The high degree of hydrogenation activity of the nickel metal (Ni(0)) particles is believed to arise, at least in part, from the properties of the nickel metal crystallites forming the particles. The inventive nickel metal (Ni(0)) particles can be composed of crystallites, regions of local crystalline order within the larger, disordered particle, wherein an average crystallite size (diameter) can be no greater than about 20-25 nm. More preferred nickel metal (Ni(0)) particles can include nickel crystallite sizes with diameters in the range of 0.1 to 10 nm.

The nickel metal (Ni(0)) particles can have on average have at least about 5×10$^{16}$ surface crystallites (e.g., instead of 10$^{16}$ surface crystallites) of size C10 or less per gram nickel. The nickel metal (Ni(0)) particles can have on average have at least about 10$^{17}$ surface crystallites (e.g., instead of 10$^{16}$ or 5×10$^{16}$ surface crystallites) of size C10 or less per gram nickel. The nickel metal (Ni(0)) particles on average can have at least about 2×10$^{15}$ surface crystallites per gram nickel, or about 10$^{15}$ surface crystallites per gram nickel. The surface crystallites per gram nickel can be calculated for substantially cuboidal crystallites, or for substantially spherical crystallites. On average per gram the heterogeneous catalyst can have at least about 2×10$^{15}$ surface crystallites per gram nickel as calculated for cuboidal crystallites, or at least about 10$^{15}$ surface crystallites per gram nickel as calculated for substantially spherical crystallites, or both.

In addition, the nickel crystallite size distribution span can be greater than 1.5. Crystallite size is typically measured as a diameter of the crystallite, for example, along the major dimension.

Other physical properties that the nickel metal (Ni(0)) particles can have include those where at least 10% of the particles have a diameter (D10) of no greater than about 6 μm or preferably no greater than about 4 μm. The surface characteristics of the nickel particles composed of the crystallites can be such that the nickel metal (Ni(0)) particles have a ratio of BET Specific Surface Area to D10 of about 0.3×10$^6$ m/gm to about 10.0×10$^6$ m/gm, or about 0.5×10$^6$ m/gm to about 5×10$^6$ m/gm.

The nickel metal (Ni(0)) particles can be substantially dry, for example, a powder or particulate form. The nickel metal (Ni(0)) particles can be suspended, dissolved or partially dissolved in a solvent. The solvent is typically a non-aqueous solvent. The solvent can be an organic solvent. For example, the solvent for the nickel metal (Ni(0)) particles can be branched or unbranched C2-C20 hydrocarbon with one or more double bonds. The solvent for the nickel metal (Ni(0)) particles can be an organonitrile liquid such as a branched or unbranched C2-C20 alkyl or alkylene substituted by at least one nitrile (CN) group. Examples of solvent include pentenenitriles such as 2-pentenenitrile, 3-pentenenitrile, 4-pentenenitrile, 2-methyl-3-butenenitrile, and 2-methyl-2-butenenitrile.

The nickel metal (Ni(0)) particles can be substantially pure nickel metal in dry form or suspended or dissolved in a solvent. For example, the nickel metal (Ni(0)) particles can be isolated without, or be substantially free of, an associated ion (e.g., without an anion) or metal (e.g., without aluminum, copper, tungsten, zinc and/or iron). The nickel metal (Ni(0)) particles can be substantially free of impurities such as carbon-containing, silicon-containing and/or nitrogen-containing moieties and/or compounds. The nickel metal (Ni(0)) particles can be substantially free of impurities such as sodium, calcium, magnesium, potassium, aluminum, or a combination thereof. For example, the nickel metal (Ni(0)) particles can have less than 10% impurities, or less than 7 wt % impurities, on a nickel basis, optionally not including sulfur as an impurity, or less than 5% impurities, or less than 4% impurities, or less than 3% impurities, or less than 2% impurities, or less than 1% impurities, or less than 0.7% impurities, or less than 0.6% impurities, or less than 0.5% impurities, or less than 0.4% impurities, or less than 0.3% impurities, or less than 0.2% impurities, or less than 0.1% impurities, or less than 0.07% impurities, or less than 0.05% impurities, or less than 0.03% impurities, or less than 0.01 wt % impurities, or less than 0.001 wt % impurities, wherein the impurities can include any suitable impurity, such as sodium, potassium, aluminum, or a combination thereof. Other than their sulfur content, the nickel metal (Ni(0)) particles can be 95% to 99.9% pure, or 98% to 99.99% pure.

The nickel metal particles can have any suitable sulfur content, wherein the sulfur can be in any suitable form, such as about 0.001 wt % to about 10 wt %, on a nickel basis, about 0.01 wt % to about 3 wt %, or about 0.01 wt % to about 3 wt %, or 10 wt % or less, or less than, equal to, or greater than about 9 wt %, 8, 7, 6, 5, 4, 3, 2.5, 2, 1.5, 1.4, 1.3, 1.2, 1.1, 1, 0.9, 0.8, 0.7, 0.6, 0.5, 0.4, 0.3, 0.2, 0.1, 0.01, or about 0.001 wt % or less.

The following Examples demonstrate the present invention and its capability for use. Several details and features are capable of modification in various apparent respects, without departing from the scope and spirit of the present invention. Accordingly, the Examples are to be regarded as illustrative in nature and non-limiting.

The Examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for.

EXAMPLES

Example 1. Calcination of Basic Nickel Carbonate

This Example illustrates use of air or nitrogen for calcination of basic nickel carbonate obtained from commercial source A.

Basic nickel carbonate is subjected to calcination in a batch rotary processor at 450° C. with gas flow rate of 3 L/min of pure gas (either air or nitrogen). When performing calcination in air (BK1), the basic nickel carbonate is subjected to calcination for 15 minutes after the concentration of carbon dioxide ($CO_2$) at the exit goes to zero.

When performing calcination in nitrogen (BK2), the basic nickel carbonate is subjected to calcination for two hours after the $CO_2$ concentration went to zero.

When employing nitrogen, the calcined basic nickel carbonate product has a distinct brown color, while the air calcined was black. The yellow to brown color of the nitrogen-calcined product does not change with exposure to air at room temperature.

In a second experiment, basic nickel carbonate was subjected to calcination in nitrogen using a rotary processor at 450° C. with nitrogen gas flow rate of 3 L/min until the concentration of carbon dioxide ($CO_2$) in the exit reached zero (BK3). The product color is brown. Air was then added to the rotary processor at 450° C. The product then changed in color from brown to black over time.

A third experiment, basic nickel carbonate was subjected to calcination in air using a rotary processor at 450° C. with nitrogen gas flow rate of 6 L/min for the following time periods after the concentration of carbon dioxide ($CO_2$) in the exit gases reached zero: for 15 minutes for one batch, and for 30 minutes for a second, separate batch. The product for both batches was NiO, which was black in color and free-flowing.

The properties of nickel oxide formed from basic nickel carbonate calcined under the indicated conditions are shown in Table 2.

TABLE 2

Properties of nickel oxide generated from BNC under various conditions.

| ID | Processing Conditions Cal. ° C. | Est. Cal. ° C. | Red ° C. | Residence Time Calcination (min) | BET SSA (m2/g) NiO | Ni | Inert Levels (% Ni) | Weight Loss at 600° C. |
|---|---|---|---|---|---|---|---|---|
| T1 | 450 | 315 | 350 | 44 | 227 | 8.84 | 3.17 | 11.38% |
| T2 | 450 | 315 | 350 | 28 | 224 | 9.9 | 3.86 | 11.16% |
| T3 | 450 | 315 | 350 | 37 | 186 | 9.45 | 3.14 | 10.34% |
| T4 | 550 | 435 | 350 | 45 | 80 | | 2.71 | 3.89% |
| T5 | 550 | 435 | 350 | 74 | 95 | 8.62 | 1.86 | 4.23% |
| T6 | 550 | 435 | 350 | 23 | 89 | 9.12 | 3.00 | 3.73% |
| T7 | 550 | 435 | 350 | 30 | 83 | 8.20 | 3.29 | 2.98% |

These experiments show that calcination of basic nickel carbonate in air at about 450° C. until carbon dioxide and water is no longer detected in the effluent is an economical and effective process for generating a NiO product that can be reduced to nickel metal.

The conversion of basic nickel carbonate to nickel oxide varies somewhat with the temperature of calcination. Table 3 shows the percent BNC converting to nickel oxide as detected by weight loss.

TABLE 3

Percent Conversion of BNC to NiO.

| Calcination Temperature (° C.) | % Conversion of BNC |
|---|---|
| 300° C. | 91.6% |
| 400° C. | 94.6% |
| 450° C. | 96.9% |
| 500° C. | 98.5% |

As shown in Table 3, calcination temperatures above at least 400° C. generally improves conversion of BNC to nickel oxide.

Example 2. Reduction of NiO in Hydrogen with Steam

This Example describes experiments that further explore reduction of NiO by hydrogen within a rotary processor in the presence of steam. The NiO for these experiments is generated by calcination of basic nickel carbonate from commercial source A or commercial source B Contact between the two phases, i.e., solid and gas phase, is accomplished in a batch rotating bed. The system operated in a semi-batch mode where a set amount of raw material charged to the kiln was continuously exposed to a flowing reactant gases.

In a first experiment (BK4), nickel oxide (250 g) is generated by calcination of BNC from commercial source A. The nickel oxide is reduced in a rotary processor at 350° C. in an atmosphere of 10% hydrogen and 30% steam with the remainder as nitrogen. The steam is added gradually (about 0.25 L increments every 1-2 minutes). The flow rate of the gaseous atmosphere through the rotary processor is 3-6 L/minute. The rotational speed of the rotary processor is 1-2 rpm. As soon as the hydrogen was introduced, the color of the material in the rotary processor changes from black to yellow and then to brown within 1-2 minutes, usually beginning at the region first contacted by hydrogen. All of the material in the bed turns brown within 15-30 minutes, but as the reaction progresses, the material eventually turns black. Hydrogen consumption is roughly 50% of the inlet value.

Buildup is observed on the wall near the end of the reactor, but most of the reduced material is free-flowing. The product is generally pebbly, where the pebbles are about 0.25 inches in diameter, or smaller. Some pebbles are larger (about ⅜ to ½ inch in size). The pebbles are friable and fall apart with some shaking to form a loose powder. When a portion of the final product is removed and exposed to air, it ignites spontaneously in air (i.e. was pyrophoric), but only after some delay.

A series of experiments is similarly performed to evaluate the reduction of nickel oxide by hydrogen in the presence of steam. The nickel oxide is generated by calcination of basic nickel carbonate from commercial source A or commercial source B at 450° C. in air. During reduction of the nickel oxide, the steam concentration is varied between 10%-50% (v/v), while the hydrogen content is varied between 10%-70% v/v.

Table 4 shows the conditions correlated with agglomeration or the lack thereof.

TABLE 4

Properties of nickel metal Ni(0) generated from nickel oxide (NiO) by hydrogen in the presence of hydrogen and steam. Nitrogen was present as the remainder of the atmosphere.

| ID | Reduction Temperature | Gas Composition | Physical Properties |
|---|---|---|---|
| BK4 | 350° C. | 10% $H_2$ 30% Steam | Free-flowing powder with friable pebbles. |
| BK5 | 350° C. | 10% $H_2$ 50% Steam | Mostly free-flowing; two large friable chunks. |
| BK6 | 350° C. | 30% $H_2$ 30% Steam | Free-flowing powder with friable pebbles. |
| BK7 | 350° C. | 70% $H_2$ 30% Steam | Free-flowing powder with friable pebbles. |
| BK14 | 400° C. | 70% $H_2$ 30% Steam | Large agglomerates. |
| BK16 | 375° C. | 70% $H_2$ 30% Steam | Agglomerates; material sticking to the wall. |
| BK18 | 375° C. | 30% $H_2$ 30% Steam | Agglomerates. |

Example 3: Reduction of Nickel in a Rotary Processor without Steam

This Example shows that nickel oxide (NiO) is more effectively reduced in a rotary processor in an atmosphere that does not use steam.

In a first experiment (BK8), nickel oxide obtained from commercial source A is reduced within a rotary processor at 350° C. in an atmosphere of 70% hydrogen and 30% nitrogen, without added steam or water. The material in the rotary reactor is initially free-flowing but then appeared to be slightly cohesive. The material builds up along the walls of the reactor until it rotates to the top of the reactor, at which time the material falls under its own weight. Eventually the material becomes less cohesive with time and starts rolling freely.

Reduction for this first experiment is complete within 1.25 hours. The final product is freely flowing, and although some pebbles are present, most are below 0.25 inches in size. Initially it appeared that the smaller pebbles (about 2-3 mm) are not friable, however after transferring the samples to an air-tight container the pebbles are not present. A sample of the Ni(0) metal so produced is very pyrophoric.

In a second experiment (BK9), nickel oxide from commercial source A is reduced within a rotary processor at 300° C. in an atmosphere of 70% hydrogen (v/v) and 30% nitrogen (v/v), without steam. Reduction is complete by about 2 hours. The nickel metal product is free-flowing and very powdery. Although some pebbles are present, they were friable. The nickel so produced is pyrophoric.

Example 4: Nickel Metal Produced with Added Sulfur

The Example illustrates that nickel metal (Ni(0)) is readily generated from nickel(II)-containing particles that contained sulfur.

In a first experiment (BK10), basic nickel carbonate (300 g) from commercial source B is mixed with 1 wt % sulfur on a final expected nickel basis, and subjected to calcination at 450° C. in air (flowing at 6 L/min). The reactor is cooled and the reaction chamber was purged of air using nitrogen. The calcined material is powdery and flowable.

The calcined material is then reduced at 350° C. in the rotary processor with an atmosphere of 70% $H_2/N_2$ as reductant (flowing at 6 L/min), and with a rotational speed of 1 rpm. During reduction the material initially turns a dirty yellow color but as the reaction progresses the powdery material begins to turn from grey to black. After reduction a few yellow flakes is visible. The nickel metal so produced is flowable.

In another experiment (BK11), NiO from commercial source C containing 1% sulfur is reduced at 350° C. in the rotary processor with an atmosphere of 70% $H_2$ and 30% $N_2$ as reductant (flowing at 6 L/min), and with a rotational speed of 1 rpm. The nickel metal product so produced is flowable and exhibits pyrophoricity.

The conditions used to form the nickel products are shown in Table 5.

TABLE 5

Nickel Metal Generated from BNC with 1% Sulfur.

| ID | Reduction Temperature | Gas Composition* |
|---|---|---|
| BK10 | 350° C. | 70% $H_2$ |
| BK11 | 350° C. | 70% $H_2$ |

As shown in Table 5, a metal product is generated from a basic nickel carbonate staring material that contains about 1% sulfur (based on the nickel content).

Example 5. Nickel Metal Produced from Nickel Formate in this experiment (BK13), nickel formate is subjected to calcination at 300° C. in nitrogen (flowing at 6 L/min) in a rotary processor with a rotational speed of 1 rpm. The product is black and very free-flowing. The nickel metal has about 3.9% inert material.

Example 6: Properties of Nickel Metal Generated Under Different Conditions

A comparison of the agglomeration/flowing properties of batches of nickel(II) particles reduced in the rotary processor with and without steam is shown in Table 6.

TABLE 6

Properties of nickel metal Ni(0) generated under Various Conditions. Nitrogen was present as the remainder of the atmosphere in the rotary processor.

| ID | Reduction Temperature | Gas Composition* | Physical Properties |
|---|---|---|---|
| BK4 | 350° C. | 10% $H_2$ 30% Steam | Commercial source A basic nickel carbonate calcined to produce NiO, which was reduced to generate a free-flowing powder with friable pebbles. |
| BK5 | 350° C. | 10% $H_2$ 50% Steam | Commercial source A basic nickel carbonate calcined to produce NiO, which was reduced to generate a mostly free-flowing product but with two large friable chunks. |
| BK6 | 350° C. | 30% $H_2$ 30% Steam | Commercial source A basic nickel carbonate calcined to produce NiO, which was reduced to generate a free-flowing powder with friable pebbles. |
| BK7 | 350° C. | 70% $H_2$ 30% Steam | Commercial source A basic nickel carbonate calcined to produce NiO, which was reduced to generate a free-flowing powder with friable pebbles. |
| BK8 | 350° C. | 70% $H_2$ | Commercial source A basic nickel carbonate calcined to produce NiO, which was reduced to generate a free-flowing powder; slight buildup that falls to loose powder. |
| BK9 | 300° C. | 70% $H_2$ | Commercial source A basic nickel carbonate calcined to produce NiO, which was reduced to generate a free-flowing powder. Takes longer for reduction compared to BK8. |
| BK10 | 375° C. | 70% $H_2$ 30% Steam | BNC from commercial source B + 1% sulfur (nickel basis) was calcined at 450° C., and the resulting NiO then reduced to yield agglomerates with material sticking to the wall. |
| BK11 | 350° C. | 70% $H_2$ | NiO from commercial source C + 1% sulfur was reduced to generate a flowable powder with friable pebbles. |
| BK12 | 400° C. | 70% $H_2$ | NiO from commercial source A was reduced to yield large agglomerates; shaking does not break apart the pebbles. |
| BK13 | 300° C. | $N_2$ only | Nickel formate was subjected to reduction in nitrogen (only) with about 68% weight loss, yielding a very free flowing product with some soft agglomerates that were easily broken. |
| BK14 | 400° C. | 70% $H_2$ 30% Steam | Large agglomerates. |
| BK15 | 375° C. | 70% $H_2$ | Bed agglomerates. |
| BK16 | 375° C. | 70% $H_2$ 30% Steam | Bed agglomerates; material sticking to the wall. |
| BK17 | 375° C. | 70% $H_2$ | Bed agglomerates; material sticking to the walls of the rotary processor but fell off at the end; agglomerates did not completely break apart on shaking. |
| BK18 | 375° C. | 30% $H_2$ 30% Steam | Bed agglomerates. |
| BK19 | 375° C. | 10% $H_2$ | Bed agglomerates that fell apart easily with shaking. |

In general, for the rotary apparatus employed under the conditions described above, less agglomeration is observed when reduction was performed at temperatures lower than 375° C. (e.g., about 300° C. to 350° C.). Introduction of steam does not reduce agglomeration in the rotary processor.

Greater than 95% percent nickel oxide is converted to nickel metal during the reduction processes described herein as detected by weight loss, and the inert level analysis described below.

Higher proportions of hydrogen in the reductant gas can be employed during reduction when no steam is added, which means the reduction process proceeds faster. For example, reduction without steam proceeds within about 1-2 hours, but when steam is added the reduction process takes 4-5 hours.

In general, although reduction temperatures of about 375° C. or somewhat higher can provide a product, the product tends to become more agglomerated than when temperatures at about 360° C. or lower were employed. Use of temperatures above 375° C. is generally correlated with more agglomeration, which can render the product unusable.

Use of hydrogen as the reductant without addition of steam is a more efficient, less wasteful process for reduction of nickel(II).

The following Table 7 shows the effect of additional process steam during reduction on the BET surface area and unconverted nickel oxides within the final resulting nickel. The additional steam is in excess of what is being generated in the reduction process due to chemistry. One can observe a trend towards lower surface area with higher steam concentration. Higher steam concentrations also leads to ineffective conversion of the nickel oxide to nickel which is indicated by insoluble nickel content which contains mostly unconverted nickel oxides. As such addition of steam is detrimental to the quality of our final nickel product and the existing process (rotary kiln) has a distinct advantage over fluidized bed for reducing nickel oxide to nickel as the fanner that does not need any additional steam to make a free flowing nickel product.

TABLE 7

Effect of steam on the measured surface area (BET) and insoluble nickel content.

| Sample ID | Reduction temperature (° C.) | Reduction gas composition (% v/v) | | | BET SSA ($m^2/g$) |
| --- | --- | --- | --- | --- | --- |
| | | $H_2$ | Steam | $N_2$ | |
| BK4 | 350° C. | 10 | 30 | 60 | 7.82 |
| BK5 | 350° C. | 10 | 50 | 40 | 7.59 |
| BK6 | 350° C. | 30 | 30 | 40 | 8.41 |
| BK7 | 350° C. | 70 | 30 | 0 | 7.29 |
| BK8 | 350° C. | 70 | 0 | 30 | 11.64 |
| BK9 | 300° C. | 70 | 0 | 30 | 10.44 |
| BK 12 | 400° C. | 70 | 0 | 30 | 10.72 |
| BK14 | 400° C. | 70 | 30 | 0 | 8.11 |
| BK15 | 375° C. | 70 | 0 | 30 | 12 |
| BK16 | 375° C. | 70 | 30 | 0 | 8.44 |
| BK17 | 375° C. | 30 | 0 | 70 | 12.2 |
| BK18 | 375° C. | 30 | 30 | 40 | 8.71 |
| BK19 | 375° C. | 10 | 0 | 90 | 11.05 |

As indicated in Table 7, when steam is present the nickel metal product has a lower BET SSA ($m^2/g$) value. For example, particulate nickel products are produced with BET SSA ($m^2$/gram) values of at least 10 $m^2$/gram when no steam is present during reduction. However, when steam is added to the reduction process, the nickel product has BET SSA ($m^2$/gram) values of less than 9 $m^2$/gram.

Example 7. 6-Inch Fluidized Bed Operation (Comparative)

About 8 lbs of basic nickel carbonate from commercial source A is charged to a 6-inch diameter fluidized bed reactor. The gas phase is dispersed in the bed of particles with an upward-flowing mode. The BNC is calcined in 100% air fluidized at 400° C. for about 1 hour. This is followed by reduction at 400° C. in the presence of a reducing gas containing 10% $H_2$ in $N_2$ for about 2 hours. The reduced nickel product is agglomerated.

Example 8. 6-Inch Fluidized Bed Operation with Steam Addition (Comparative)

About 8 lbs of BNC from commercial source A is charged to the 6-inch diameter fluidized bed reactor described in example 7. The BNC is calcined in 100% air fluidized at 400° C. for about 1 hour. This is followed by reduction at 400° C. in a reducing gas containing 10% $H_2$/10% steam/balance $N_2$ for about 2 hours. The reduced nickel product is not agglomerated and instead has a powdery and free-flowing consistency.

Example 9. 6-Inch Fluidized Bed Operation with Steam Addition (Comparative)

About 8 lbs of BNC from commercial source A is charged to the 6-inch diameter fluidized bed reactor described in example 7. The BNC is calcined in 20% steam in $N_2$ and at 400° C. Reduction is carried at 325° C. with a reducing gas containing 20% $H_2$/20% Steam/balance $N_2$. The final product is mostly free flowing but did have chunks/agglomerates. This example shows the effect of limiting hydrogen concentration during the reduction process compared to Example 8. Addition of steam does not eliminate the chucks and agglomerates.

Example 10: 7-Inch Diameter Rotary Unit Operation with No Steam Addition

Processing is performed in a continuous 7-inch diameter, horizontal rotary kiln processes having a variable-speed rotation motor and adjustable incline. The unit is equipped with a feed canister, lock hopper, variable-feed screw feeder and four-zone temperature control with individual zone thermocouples. The gas feeds are metered using mass flow controllers. The off-gas exited the rotary unit and passed through a hot cyclone for entrained solid fines separation from the gas stream. The cyclone-separated gas stream is cooled using a water-cooled heat exchanger and thermally destructed in an afterburner. An infra-red gas detector [IR Analyzer 208] measures the $CO_2$ content and a thermal conductivity detector (TCD) measures the $H_2$ content of the gas before the afterburner. Contact between the two phases, i.e., solid and gas phase, is accomplished in a counter-current flow mode, where the two phases travel in opposite directions (i.e., the gas phase enters the rotary unit near the exit for the solid phase).

Basic nickel carbonate from commercial source A is calcined in the continuous 7" diameter, horizontal rotary unit at 450° C. The feed rate of BNC was 7.5 kg/hr and air flow rate is 30 L/min. The off-gas is continuously monitored for the $CO_2$ produced in the process, which is present at the level expected from the given mass of BNC calcined per unit time. The calcination end product, nickel oxide, is evaluated for any subsequent weight loss in a muffle furnace to determine the degree of conversion. The conversion is maintained above 95% for the process.

The subsequent nickel oxide product is charged back to the 7" rotary kiln (in a separate campaign) and is reduced with 70% $H_2/N_2$ at rotational speed of 1.5-3 rpm and typical incline of 0.026 ft/ft. Hydrogen is fed counter-current to the nickel oxide feed. Under this configuration, a significant amount of nickel and nickel oxide buildup is observed in the reactor. During the run, product discharge is erratic and poor. At the end of the run about 40 lbs of nickel-nickel oxide is present inside the reactor. Build-up on wall effectively lead to heat transfer issues. The volume occupied by the build-up is approximately 30% of the kiln volume and is unmanageable. The process was terminated and the rotary kiln is cleaned out.

By placing adequate lifters which are about 0.25" in width and about 0.75" in height and welded as strips running parallel, but in slightly "cork-screw" fashion along the interior length of the kiln, the material in the kiln moves more efficiently. The "cork-screw" curve of the lifters is such that the horizontal position of each lifter at one end of the kiln is at approximately 15° from the horizontal position of that lifter at the other end of the kiln. Thus, the strip starts at the front end of kiln at a 6 o'clock position and ends at the back end at about a 5 o'clock position, with a slight curve over the approximate 6 ft length of kiln in the direction of the kiln rotation. The lifters provide a forward momentum to the powder.

The movement of the particles is significantly improved when a mechanical agitation to the kiln is provided which involved using a set of rapping mechanisms outside of the kiln on each side of the furnace. The rotation of the kiln caused the rappers to knock on the reactor vessel at regular frequency of about 10-12 seconds in sequence at front and back end of the kiln. The material in the kiln moves efficiently through the kiln and the amount in the kiln is reduced to approximately 3-5 lbs occupying about 5-10% of the reactor volume. Product discharge rate is steady and consistent. The off-gas $H_2$ concentration also becomes more uniform.

Example 11. 7-Inch Diameter Rotary Unit Operation with No Steam Addition

BNC from commercial source A is calcined in a continuous 7" rotary unit at 450° C. as described in Example 10.

The resulting nickel oxide is then reduced in the same continuous rotary unit in a subsequent reduction campaign. The reduction temperature is 310-340° C. The reducing gas composition is 60-70% $H_2/N_2$, typically at 70%. No additional steam is introduced in the process. Residence time of the particles is varied between 40-125 minutes, typically about 75 minutes. The solid feed rate is varied between 1.0-5 kg/hr, typically at 1.5 kg/hr. The hydrogen/NiO molar feed rate is maintained between values of 1-3, typically at 2.4. The gas residence time is varied between 1-5 minutes, typically at 1.4 minute. The rotary kiln rpm is varied between 0.5-5, the value of 3 rpm giving the adequate mixing of particles with gas. The gas flow is introduced counter-current to the particle flow. This counter-current configuration is usually preferred to keep the dust from being carried with the product but one can envision using co-current flow of both gas and particles to achieve the same end. The counter-current flow is also desired from the point of view of keeping highest concentration of hydrogen seeing the lowest concentration of nickel oxide at its entrance. This minimizes a need for high temperatures and reduces the likelihood of hot spots due to the exothermic reduction of nickel oxide with hydrogen.

The off-gas is monitored for the hydrogen concentrations and is found to give hydrogen levels within expected level (~43%) based on the mass feed rate of oxide. Greater than 95% conversion of nickel oxide to reduced nickel is achieved. Steady product discharge rate is accomplished. The final product has low inert levels of about 4% or less.

Example 12. 7-Inch Diameter Rotary Unit Operation with No Steam Addition

Calcination of BNC from commercial source A is performed using the same conditions and rotary unit as described in Example 10. The reduction is performed with 40% $H_2/N_2$. The hydrogen to NiO feed ratio is 1.4, which is about 40% in excess of stoichiometric requirements. However, the amount of hydrogen in the off-gas does not reach the expected value indicating not all the nickel oxide is being converted. The product that comes out of the reactor is not pyrophoric. The conversion of NiO to Ni(0) is only about 57%, indicating incomplete reduction of the final product. The hydrogen concentration in the off-gas is ~20% instead of the expected ~11%. This indicates that even though the amount of hydrogen in the feed gas relative to nickel oxide is 40% more than the theoretical stoichiometric amount required, a percentage of the gas apparently bypasses the material in the system without contacting the solids and effectively leads to incomplete conversion of nickel oxide.

This example is carried out for a set residence time. The set residence time can be increased to accommodate the lower concentrations of hydrogen in the feed, and increase the conversion of NiO to Ni(0). Alternatively, a higher percentage of hydrogen can be used to reduce the processing time and improve the percent conversion of nickel oxide to nickel.

Example 13. 7-Inch Diameter Rotary Unit Operation with No Steam Addition

Calcination and reduction of BNC from commercial source A are carried at the same conditions and rotary unit as described in Example 10. The reduction is carried out with 60% $H_2/N_2$ leading to $H_2$/NiO feed ratio of 2.1. The off-gas composition of $H_2$ is within the expected range of 33-34%. The final product has low inert levels.

Example 14. 7-Inch Diameter Rotary Unit Operation with No Steam Addition

Calcination of BNC from commercial source A is carried at the same conditions as shown in Example 10. The reduction is carried out at average temperatures of 325° C. with 70% $H_2/N_2$. The feed rate of nickel oxide is increased from 1.5 kg/hr to 2 kg/hr thereby decreasing the feed material residence time from 75 minutes to 56 minutes. The molar feed ratio of $H_2$/NiO is 1.82. The $H_2$ concentrations in the off-gas are close to the levels expected for good reduction, which is approximately 33-34%. The nickel oxide conversion to nickel is about 90-95%. The higher feed rate of nickel oxide indicates the residence time of 56 minutes is not sufficient to convert higher percentages of nickel oxide to nickel.

Table 8 summarizes the conditions used for reduction of nickel oxide in a rotary kiln. These data indicate that reduction of nickel oxide is efficiently performed at $H_2$/NiO molar ratios that are above 1.4 for residence times of about 56-75 minutes.

TABLE 8

$H_2$/NiO ratio for reduction in a rotary kiln. The $H_2$ feed rate was constant, and the NiO feed rate was adjusted.

| Run No. | Gas composition | $H_2$/NiO molar ratio |
| --- | --- | --- |
| 1 | 40% $H_2/N_2$ | 1.4 |
| 2 | 60% $H_2/N_2$ | 2.1 |
| 3 | 70% $H_2/N_2$ | 2.4 |
| 4 | 70% $H_2/N_2$ | 1.8* |

Example 15: 7-Inch Diameter Rotary Unit Operation with No Steam

Calcination of BNC from commercial source A is carried at the same conditions as described in Example 1. Reduction is performed at temperatures of 350-375° C., which is higher than used in some of the previous experiments. The feed rate of nickel oxide is 1.5 kg/hr and the $H_2$/NiO molar ratio is 2.4. The residence time of the material is 75 minutes. Small chunks of material are formed during the reduction process that could be heard dropping inside the product collection canister. The temperature is maintained for approximately 6-8 hours and the chunks or agglomerate formation continued to be observed although they are not consistently produced. These chunks are about 2-5% of the total bed as assessed by eye.

Lowering the temperatures back to 300-350° C. results in disappearance of these lumps. The product recovery is stable and good. The final product exhibits low inert levels. As such the quality of the final product is not affected due to higher temperatures.

Example 16: Commercial Production of Reduced Nickel in a 2-Ft Diameter Rotary Unit with No Steam Addition This Example illustrates scaled-up production of reduced nickel using basic nickel carbonate obtained from commercial sources. Production is performed in two steps; i) calcination of basic nickel carbonate in the presence of air or nitrogen, and ii) reduction of the calcined nickel II product from i) to generate reduced nickel (Ni(0)) particles.

An industrial-scale horizontal particle processer (or kiln) is used that can provide low rpm rotation with a slightly inclined horizontal axis. The 2-ft internal diameter (ID.)× 10-ft long rotary kiln with an heated zone of about 8 ft is equipped with a feed hopper, a mechanical or pneumatic feeder such as a screw conveyor, gas feed ports (for air, $N_2$, reducing gas such as hydrogen), temperature and pressure indicators, an air-tight product discharge section, a conveyor system to remove the product, and an off-gas port to remove the spent gases. The unit can also be equipped with auxiliary systems for heating, cooling, introduction of nitrogen (as an inert gas) with control/safety interlocks during batch or continuous operation. The system is provided with a cyclone separator to remove the carry-over particles and an after-scrubber for off-gas treatment. The kiln can be electrically or gas fired.

Calcination Step: The feedstock, basic nickel carbonate, is fed to the feed hopper and conveyed into the rotary kiln at 300-400 lbs/hr rate. The solids inventory in the kiln is such that the nickel feed reaches no more than $\frac{1}{4}^{th}$ of the diameter measured vertically when the barrel is leveled. The particles' residence time is maintained in the 30-60 minutes range. The kiln is maintained at 400–500° C. internal temperature using external heat and by feeding 12-25 ft$^3$/min of gas flow (either air or nitrogen) for temperature uniformity. As the particles tumble down the rotary kiln barrel, it is subjected to the calcination conditions. The off-gas is continuously monitored for carbon dioxide [$CO_2$]. The flowing particles are completely calcined when the off-gas $CO_2$ concentration drops to zero and stays there. The calcined particles are collected at the exit of the rotary kiln and properly stored at normal dry storage conditions.

Reduction Step: The calcined material (nickel oxide) generated in the calcination step is fed into the rotary unit using an feed auger system, or with a hopper and star valve feeder, or any suitable continuous feed mechanism. The nickel oxide feed could run co-current or counter-current to the gas flow. The example below employs counter-current flow of material.

The particles residence time is maintained in the 60-120 minutes range. The kiln is maintained at 300-350° C. internal temperature using external heat and by feeding 15-25 ft$^3$/min of gas flow, a mixture of 60-70% (v/v) hydrogen/nitrogen. There is no addition of water or steam to the kiln. Reduction is performed by the reducing gas as the material tumbles down the barrel and is internally dispersed in the continuous gas-phase. At the end of the reduction step, the free-flowing, powdery reduced nickel is removed from the kiln under nitrogen atmosphere.

The reduced nickel is transferred to an air-tight container for proper storage. A sample of the reduced Ni(0) metal so produced is very pyrophoric and shows high reactivity in lab testing.

Example 17 (Comparative). Hydrogenation of Dinitriles Over Sponge-Type Nickel Catalyst 60 grams of Raney® brand nickel sponge metal catalyst in dilute aqueous NaOH is added to a two-liter autoclave under nitrogen blanketing. The catalyst is rinsed with two autoclave volumes of distilled water and two autoclave volumes of dry adiponitrile. The autoclave is equipped with a gas sparger at the bottom and a pressure control vent at the top. Dry nitrogen is circulated through the sparger and hydrogen is gradually added to bring pressure to 35 psig, set at the pressure control vent. Temperature gradually increases to about 150° C., at which point the hydrogen charged is shut off and the autoclave is vented under nitrogen blanketing. Samples are drawn and analyzed for conversion of adiponitrile to diamines and for selectivity to the desired hexamethylenediamine.

Example 18. Hydrogenation of Dinitriles Over Nickel Particles of Example 16

Example 17 is repeated with 60 grams of the nickel metal produced in Example 16, except that a continuous stirred tank reactor ("CSTR") is used for the reaction vessel with 100% recycle.

Example 19. Hydrogenation of Dinitriles Over Nickel Particles of Example 16

Example 18 is repeated with 60 grams of the nickel metal produced in Example 16. The recycle is reduced from 100% to 20% after hydrogen pressure is increased to 35 psig. Make-up mixture is charged to the CSTR on level control. After two (2) hours of operation, the CSTR is shut down. The continuously drawn product is analyzed for conversion to diamines and selectivity to the desired HMD product.

Example 20. Fluid-Bed Hydrogenation of 1,3-Butadiene Over Nickel Articles of Example 16

The catalyst of Example 16 is fluidized in a bubbling bed regime by flowing dry nitrogen through a gas distributor at the bottom of a pilot plant scale fluid bed reactor with a total reactor volume of about 100 L. Pressure is controlled at 20 psig. The 1,3-butadiene charge is added to the bottom of the reactor and hydrogen is gradually added. The hydrogenation reaction is highly exothermic, so the hydrogen charge rate is regulated to control the reaction temperature at about 300° C. The nickel catalyst, reactant, and products flow upwardly through the reactor to two stages of cyclonic separators that return the nickel catalyst to a mid-level discharge within the fluid bed, while allowing the product mixture to be recovered overhead.

Example 21. Desulfurization Over Nickel Particles of Example 16

Example 20 is repeated with a high-sulfur diesel feedstock.

Example 22. Hydrogenolysis of Esters Over Nickel Particles of Example 16

Example 20 is repeated with ethyl acetate, which was converted into ethanol.

Example 23. Hydrogenolysis of Ethers Over Nickel Particles of Example 16

Example 20 is repeated with diphenyl ether, which was converted to phenol.

Example 24. Dehalogenation Over Nickel Particles of Example 16

Example 20 is repeated with benzyl chloride, which was converted to toluene.

Example 25. Converting Aldehyde to Sorbitol Over Nickel Particles of Example 16

Example 20 is repeated with dextrose, which was converted to sorbitol.

Example 26. Converting Acetylene to Butanediol Over Nickel Particles of Example 16

Example 20 is repeated with acetylene, which was converted to butanediol.

Example 27. Converting Adiponitrile to Hexamethylenediamine Over Nickel Particles of Example 16

Example 20 is repeated with adiponitrile, which was converted to hexamethylenediamine.

Example 28. Production of Nickel Particles

Figure 2:
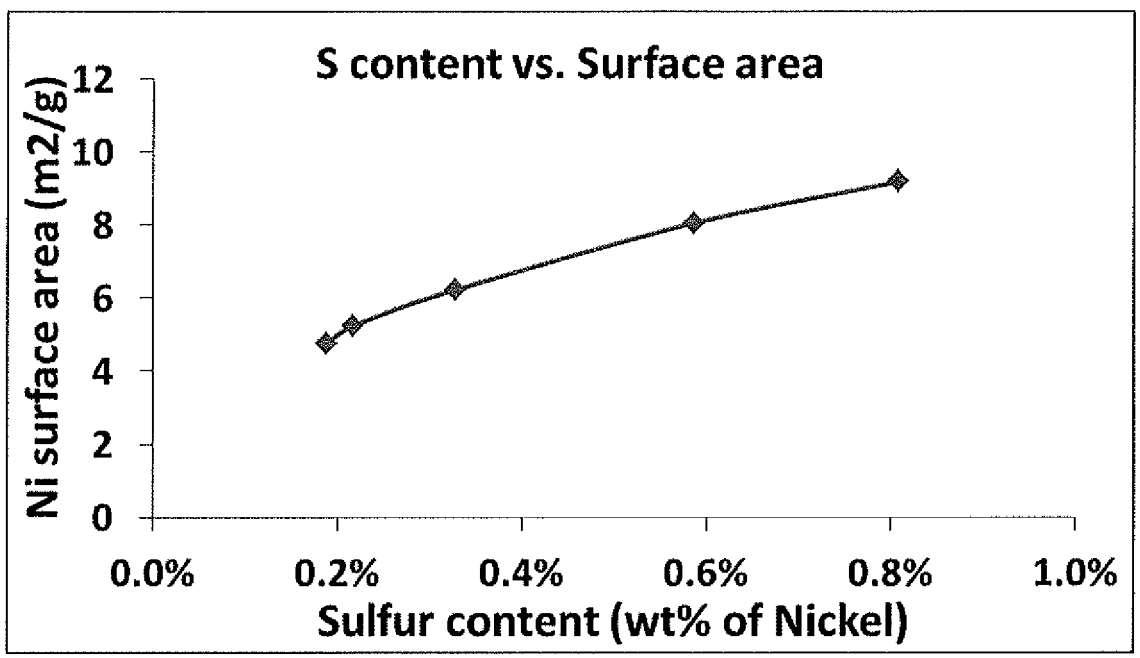
FIG. 2 illustrates nickel surface area versus sulfur content, in accordance with various embodiments.

Commercial nickel oxide procured from Metals and Materials Processing (MMP), NC, having a starting sulfur concentration of 0.2 wt % on a nickel basis, was reduced to nickel at 350° C. The as-produced nickel was evaluated for BET surface area which was 4.0 m$^2$/g. Added variable amount of elemental sulfur to the nickel oxide to give sulfur composition of 0.2 wt % to 0.8 wt % on nickel basis under identical conditions as mentioned above. The surface area increased to ~9.2 m$^2$/g at 0.81% sulfur content. FIG. 2 illustrates the nickel surface area versus the sulfur content on wt % nickel basis.

Example 29. Production of Nickel Particles

Figure 3:
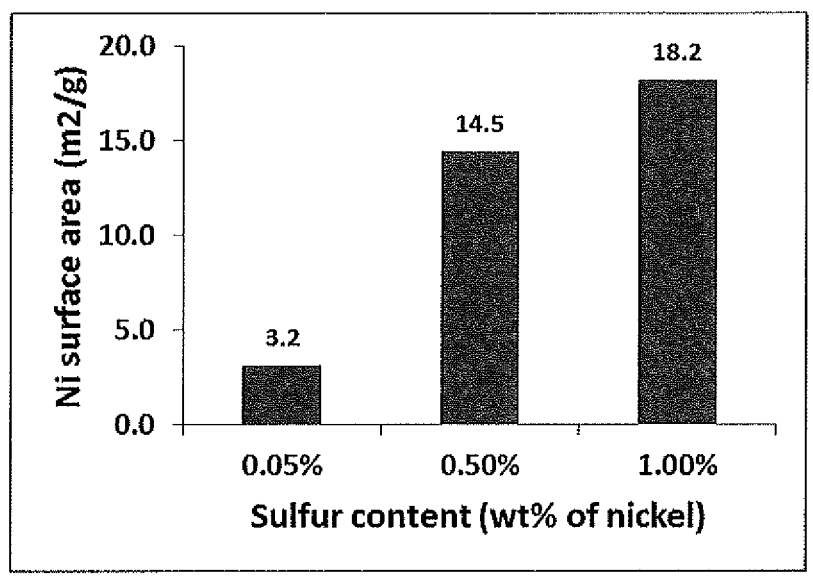
FIG. 3 illustrates the nickel surface area versus sulfur content on a wt % nickel basis, in accordance with various embodiments.

Queensland basic nickel carbonate procured from Metchem, N.C. was first calcined to generate nickel oxide. The calcination was carried out at 400° C. in a packed bed reactor. The produced nickel oxide had a sulfur concentration of 0.05 wt % on a nickel basis. To the produced nickel oxide was added quantities of elemental sulfur up to 1 wt % on a nickel basis and reduced at 300-350° C. to produce nickel with doped sulfur. The raw material nickel oxide has sulfur concentrations of 0.05 wt % on a nickel basis. FIG. 3 illustrates the nickel surface area versus sulfur content on a wt % nickel basis.

Example 30. Production of Nickel Particles

Figure 4:
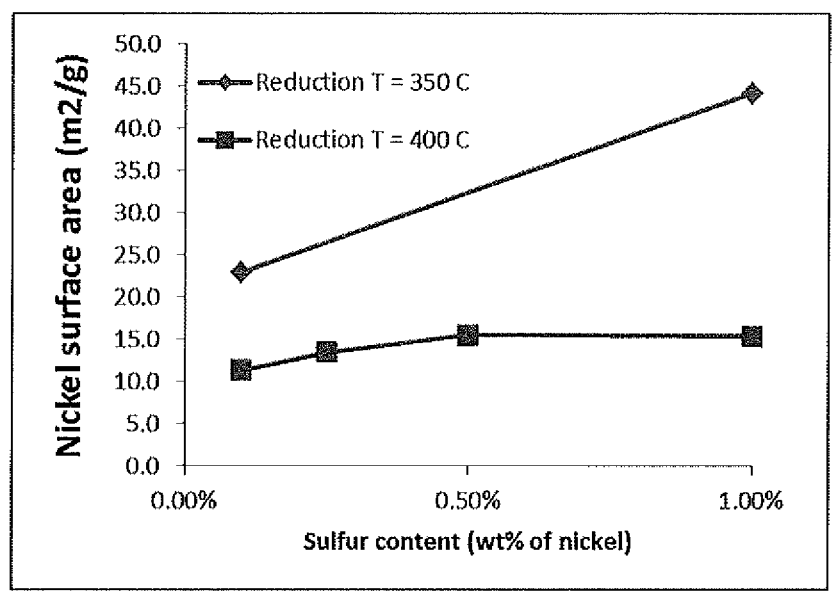
FIG. 4 illustrates nickel surface area versus sulfur content, in accordance with various embodiments.

Commercial BNC was procured from Umicore which had about 800-1000 ppm of silica and about 800 ppm of sulfur by weight of nickel. The BNC was calcined at 400° C. to generate nickel oxide. The nickel oxide was doped with sulfur with varying concentrations and reduced at either 350° C. or 400° C. The effect of addition of sulfur is shown in FIG. 4. The higher surface area without sulfur addition is attributed to the presence of silica. The higher reduction temperatures of 400° C. led to agglomeration and caused a lower surface area overall.

REFERENCES

U.S. Pat. No. 3,793,005 discloses a process for reducing oxides and compounds heat decomposable to oxides of nickel and cobalt. A refractory lined hearth to form a shallow bed of pellets in a static state was used in the '005 patent process. The bed was heated to a temperature between about 750° C. and 1,100° C. by radiation and convection. The '005 patent also discloses incorporation of a reducing reagent within briquettes of nickel oxide.

U.S. Pat. No. 3,656,934 relates to the reduction of nickel-containing lateritic ores in a rotary kiln at high production rates to achieve selective reduction of nickel contained in the ore wherein the ore is preheated to at least about 1,000° F. (538° C.).

Rhamdhani et. al., Proceedings of EMC, pp. 899-913 (2009), discloses phenomena affecting the final-product during the reduction of basic nickel carbonate (BNC) and NiO as the following: (1) chemical changes, i.e., decomposition, reduction and oxidation reactions; (2) NiO and Ni recrystallization and grain growth; (3) NiO and Ni sintering and densification; and (4) agglomeration of the NiO and Ni particles. Some of the disadvantages of the BNC and NiO reduction process described in Rhamdhani et. al., are: (i) saw dust is added to provide sufficient porosity in the bed during the reduction process, (ii) the reduction is carried out at an average temperature of 900° C. under an atmosphere containing cracked ammonia, 75% H$_2$ and 25% N$_2$; and (iii) the reduction product is crushed, blended with stearic acid and the pressed compacts undergo another sintering operation to produce >99% Ni.

U.S. Pat. No. 2,000,171 describes a multiple hearth type reactor where reduction of nickel ores was carried out by heating the material in a reducing environment using water gas mixture at 400-550° C. The patent discloses that the difficulty with reducing the nickel ore is the formation of cake of sintered material which was alleviated by adding the reducing gases at high temperatures of 500-700° C.

Additional Embodiments

The following exemplary embodiments are provided, the numbering of which is not to be construed as designating levels of importance:

Embodiment 1 provides a method of making a hydrogenation catalyst comprising particulate nickel metal (Ni(0)), the method comprising:

calcining first nickel(II)-containing particles in an atmosphere comprising oxidizing constituents to generate second nickel(II)-containing particles; and reducing the second nickel(II)-containing particles in a reducing atmosphere while rotating or turning the second nickel(II)-containing particles at about 275° C. to about 360° C. for a time sufficient to generate the particulate nickel metal (Ni(0)), wherein the particulate nickel metal (Ni(0)) is free flowing.

Embodiment 2 provides the method of Embodiment 1, wherein neither water nor steam are added to the reducing atmosphere.

Embodiment 3 provides the method of any one of Embodiments 1-2, wherein the second nickel(II)-containing particles are substantially free of water.

Embodiment 4 provides the method of any one of Embodiments 1-3, wherein the second nickel(II)-containing particles comprise basic nickel carbonate, nickel oxide, nickel carbonate, nickel bicarbonate, nickel oxalate, nickel formate, nickel squarate, nickel hydroxide, nickel nitrate, nickel cyanate, nickel sulfate and combinations thereof.

Embodiment 5 provides the method of any one of Embodiments 1-4, wherein calcining comprises heating the first nickel(II)-containing particles in an atmosphere comprising the oxidizing constituents at a temperature of about 350° C. to about 600° C. for a time sufficient to remove volatile components from the first nickel(II)-containing particles.

Embodiment 6 provides the method of Embodiment 5, wherein the time sufficient to remove volatile components from the first nickel(II)-containing particles is about 10 minutes to six hours.

Embodiment 7 provides the method of any one of Embodiments 1-6, wherein the second nickel(II)-containing particles do not collide with sufficient force to agglomerate during the reducing.

Embodiment 8 provides the method of any one of Embodiments 1-7, wherein the second nickel(II)-containing particles are not compressed with sufficient force to agglomerate during the reducing.

Embodiment 9 provides the method of any one of Embodiments 1-8, wherein rotating or turning comprises rolling, stirring, falling, mixing, vibrating, or a combination thereof.

Embodiment 10 provides the method of any one of Embodiments 1-9, wherein the reducing is performed in a rotary kiln processor.

Embodiment 11 provides the method of any one of Embodiments 1-10, further comprising knocking the reaction vessel in at least one location.

Embodiment 12 provides the method of any one of Embodiments 1-11, wherein the reducing atmosphere contains hydrogen ($H_2$) as reductant, and optionally a carrier gas as the remainder of the atmosphere.

Embodiment 13 provides the method of any one of Embodiments 1-12, wherein the reducing atmosphere is about 1 mol % to about 100 mol % hydrogen.

Embodiment 14 provides the method of any one of Embodiments 1-13, wherein a $H_2$/Ni molar ratio is employed during the reducing of between about 1.0 and about 2.5.

Embodiment 15 provides the method of any one of Embodiments 1-14, wherein a $H_2$/Ni molar ratio is employed during the reducing that is greater than about 2.

Embodiment 16 provides the method of any one of Embodiments 1-15, wherein the time sufficient to generate the free-flowing particulate nickel metal (Ni(0)) product during the reducing is about 0.5 hour to about 3 hours.

Embodiment 17 provides the method of Embodiment 16, wherein the first nickel(II)-containing composition is prepared by contacting nickel(II) ions dissolved in water with carbonate ions, bicarbonate ions, or a combination of carbonate ions and bicarbonate ions.

Embodiment 18 provides the method of any one of Embodiments 1-17, wherein the particulate nickel (Ni(0)) product has a BET SSA ($m^2$/gram) value of at least about 8 $m^2$/gram.

Embodiment 19 provides the method of any one of Embodiments 1-18, wherein the nickel(II)-containing particles are substantially free of aluminum, potassium, and sodium.

Embodiment 20 provides the method of any one of Embodiments 1-19, further comprising adding sulfur to the first nickel(II)-containing particles, the second nickel(II)-containing particles, or a combination thereof.

Embodiment 21 provides the method of Embodiment 20, wherein the added sulfur is elemental sulfur.

Embodiment 22 provides the method of any one of Embodiments 1-21, wherein at the time of the calcining the first nickel(II)-containing particles are about 0.001 wt % to about 10 wt % sulfur, on a nickel basis.

Embodiment 23 provides the method of any one of Embodiments 1-22, wherein at the time of the calcining the first nickel(II)-containing particles are about 0.01 wt % to about 3 wt % sulfur on a nickel basis.

Embodiment 24 provides the method of any one of Embodiments 1-23, wherein at the time of the reducing the second nickel(II)-containing particles are about 0.001 wt % to about 10 wt % sulfur, on a nickel basis.

Embodiment 25 provides the method of any one of Embodiments 1-24, wherein at the time of the reducing the second nickel(II)-containing particles are about 0.01 wt % to about 3 wt % sulfur, on a nickel basis.

Embodiment 26 provides a hydrogenation catalyst comprising particulate nickel metal (Ni(0)) formed by the method of any one of Embodiments 1-25.

Embodiment 27 provides a method of hydrogenation comprising:

contacting a starting material with the hydrogenation catalyst comprising particulate nickel metal (Ni(0)) formed by the method of any one of Embodiments 1-26 under conditions sufficient to hydrogenate the starting material.

Embodiment 28 provides the method of Embodiment 27, wherein the hydrogenation of the starting material comprises at least one of hydrogenation of an unsaturated compound, reductive alkylation of a carbonyl compound with an amine, hydrogenolysis of an ester or ether, dehydrogenation of a hydrocarbon or alcohol, dehalogenation, desulfurization, or a combination thereof.

Embodiment 29 provides the method of any one of Embodiments 27-28, wherein the hydrogenation of the starting material comprises at least one of reduction of a nitro group to an amine group, reduction of a nitrile to an amine, reduction of an aldehyde to an alcohol, reduction of an olefin to a paraffin, reduction of an alkyne to a paraffin, and reduction of an aromatic compound to an aliphatic compound.

Embodiment 30 provides a heterogeneous catalyst comprising particulate nickel metal (Ni(0)) formed by a method comprising:

calcining first nickel(II)-containing particles in an atmosphere comprising oxidizing constituents to generate second nickel(II)-containing particles; and reducing the second nickel(II)-containing particles in a reducing atmosphere while rotating or turning the second nickel(II)-containing particles at about 275° C. to about 360°

C. for a time sufficient to generate the particulate nickel metal (Ni(0)), wherein the particulate nickel metal (Ni(0)) is free-flowing.

Embodiment 31 provides a heterogeneous catalyst comprising particulate nickel metal (Ni(0)), the heterogeneous catalyst comprising:
a hydrogen-reduced nickel(II)-containing particle.

Embodiment 32 provides a heterogeneous catalyst comprising particulate nickel metal (Ni(0)), the heterogeneous catalyst having a BET Specific Surface Area of about 2 $m^2/g$ to about 200 $m^2/g$, at least 10% of the particles of the heterogeneous catalyst having particle size (D10) of no greater than about 6 μm, the heterogeneous catalyst having an aluminum content less than about 1 wt % and a sodium content less than about 1 wt %.

Embodiment 33 provides a heterogeneous catalyst comprising particulate nickel metal (Ni(0)), the heterogeneous catalyst comprising nickel crystallites, wherein:
the heterogeneous catalyst has a BET Specific Surface Area of at least about 1 $m^2/g$;
at least 10% of the nickel crystallites have a size (C10) that is less than about 20 nm;
the nickel crystallites have an average crystallite size of no greater than about 100 nm; and
the nickel crystallite size distribution span is greater than about 1.0.

Embodiment 34 provides the heterogeneous catalyst of Embodiment 33, wherein the nickel metal (Ni(0)) particles have a BET Specific Surface Area/C50 ratio of not less than $0.07 \times 10^9$ m/g.

Embodiment 35 provides the heterogeneous catalyst of any one of Embodiments 33-34, wherein the nickel metal (Ni(0)) particles have a BET SSA/C50 ratio of at least about $0.1 \times 10^9$ m/g.

Embodiment 36 provides the heterogeneous catalyst of any one of Embodiments 33-35, wherein the nickel metal (Ni(0)) particles on average have at least about $10^{15}$ surface crystallites per gram of nickel.

Embodiment 37 provides the heterogeneous catalyst of any one of Embodiments 33-36, wherein at least 10% of the nickel metal (Ni(0)) particles have a size (D10) of no greater than about 6 μm.

Embodiment 38 provides the heterogeneous catalyst of any one of Embodiments 33-37 wherein the nickel metal (Ni(0)) particles have a Laser Diffraction Specific Surface Area of at least about 0.4 $m^2/g$.

Embodiment 39 provides the heterogeneous catalyst of any one of Embodiments 33-38, wherein the nickel metal (Ni(0)) particles have a BET Specific Surface Area to D10 ratio of about $0.3 \times 10^6$ m/g to about $10.0 \times 10^6$ m/g.

Embodiment 40 provides the heterogeneous catalyst of any one of Embodiments 33-39, wherein the nickel metal (Ni(0)) particles have on average at least about $10^{16}$ surface crystallites per gram nickel that are smaller than or equal to size C10.

Embodiment 41 provides the heterogeneous catalyst of any one of Embodiments 33-40, wherein the nickel metal (Ni(0)) particles have a BET Specific Surface Area of at least about 2 $m^2/g$.

Embodiment 42 provides the heterogeneous catalyst of any one of Embodiments 33-41, wherein the nickel metal (Ni(0)) particles have a BET Specific Surface Area of about 5 $m^2/g$ to about 200 $m^2/g$.

Embodiment 43 provides the heterogeneous catalyst of any one of Embodiments 33-42, wherein the nickel metal (Ni(0)) particles has a BET Specific Surface Area of about 10 $m^2/g$ to about 50 $m^2/g$.

Embodiment 44 provides the heterogeneous catalyst of any one of Embodiments 33-43, wherein the nickel crystallites have an average crystallite size of no greater than about 70 nm.

Embodiment 45 provides the heterogeneous catalyst of any one of Embodiments 33-44, wherein the nickel crystallites have an average crystallite size of no greater than about 50 mm.

Embodiment 46 provides the heterogeneous catalyst of any one of Embodiments 33-45, wherein the nickel crystallites have an average crystallite size of no greater than about 30 mu.

Embodiment 47 provides the heterogeneous catalyst of any one of Embodiments 33-46, wherein the nickel metal (Ni(0)) particles have a BET SSA/C50 ratio of at least about $0.4 \times 10^9$ m/g.

Embodiment 48 provides the heterogeneous catalyst of any one of Embodiments 33-47, wherein the nickel metal (Ni(0)) particles have an LD SSA/C50 ratio of at least about $4.3 \times 10^6$.

Embodiment 49 provides the heterogeneous catalyst of any one of Embodiments 33-48, wherein the nickel metal (Ni(0)) particles have an LD SSA/C50 ratio of at least about $10^7$.

Embodiment 50 provides the heterogeneous catalyst of any one of Embodiments 33-49, wherein at least 10% of the nickel crystallites have a size (C10) that is less than about 10 nm.

Embodiment 51 provides the heterogeneous catalyst of any one of Embodiments 33-50, wherein the nickel crystallites have an average crystallite size of no greater than about 20-25 nm.

Embodiment 52 provides the heterogeneous catalyst of any one of Embodiments 33-51, wherein the nickel crystallites have a nickel crystallite size distribution span greater than 1.5.

Embodiment 53 provides the heterogeneous catalyst of any one of Embodiments 33-52, wherein the nickel metal (Ni(0)) particles on average have at least about $2 \times 10^{15}$ surface crystallites per gram nickel.

Embodiment 54 provides the heterogeneous catalyst of Embodiment 53, wherein the surface crystallites per gram nickel are calculated for substantially cuboidal crystallites.

Embodiment 55 provides the hydrogenation catalyst of any one of Embodiments 53-54, wherein the surface crystallites per gram nickel are calculated for substantially spherical crystallites.

Embodiment 56 provides the heterogeneous catalyst of any one of Embodiments 33-55, wherein on average per gram the nickel metal (Ni(0)) particles have at least about $2 \times 10^{15}$ surface crystallites per gram nickel as calculated for cuboidal crystallites, or at least about $10^{15}$ surface crystallites per gram nickel as calculated for substantially spherical crystallites, or both.

Embodiment 57 provides the heterogeneous catalyst of any one of Embodiments 33-56, wherein the nickel metal (Ni(0)) particles have a ratio of BET Specific Surface Area to Laser Diffraction Specific Surface Area of between 20 and 30.

Embodiment 58 provides the heterogeneous catalyst of any one of Embodiments 33-57, wherein the nickel metal (Ni(0)) particles have a ratio of BET Specific Surface Area to D10 of from 3 to 5 $m^2/g/\mu m$ or about $0.5 \times 10^6$ m/g to about $5 \times 10^6$ m/g.

Embodiment 59 provides the heterogeneous catalyst of any one of Embodiments 33-58, wherein the nickel metal (Ni(0)) particles have on average at least about $10^{16}$ surface crystallites of size C10 or less per gram nickel.

Embodiment 60 provides the heterogeneous catalyst of any one of Embodiments 33-59, wherein the nickel metal (Ni(0)) particles have on average at least about $10^{17}$ surface crystallites of size C10 or less per gram nickel.

Embodiment 61 provides the heterogeneous catalyst of any one of Embodiments 33-60, wherein the heterogeneous catalyst is substantially zero-valent nickel.

Embodiment 62 provides the heterogeneous catalyst of any one of Embodiments 33-61, wherein the nickel metal (Ni(0)) particles have a sulfur content of about 0.001 wt % to about 0.001 wt % to about 10 wt %, on a nickel basis Embodiment 63 provides the heterogeneous catalyst of any one of Embodiments 33-62, wherein the nickel(II)-containing particles are about 0.01 wt % to about 3 wt % sulfur, on a nickel basis.

Embodiment 64 provides the heterogeneous catalyst of any one of Embodiments 33-63, wherein the nickel(II)-containing particles have a sulfur content of about 0.01 wt % to about 3 wt % sulfur, on a nickel basis.

Embodiment 65 provides a method of hydrogenation comprising:
contacting a starting material with the hydrogenation catalyst comprising nickel metal (Ni(0)) of any one of Embodiments 31-33 under conditions sufficient to hydrogenate the starting material.

Embodiment 66 provides the method or the hydrogenation catalyst of any one or any combination of Embodiments 1-65 optionally configured such that all elements or options recited are available to use or select from.

What is claimed is:

1. A method of hydrogenation comprising:
    contacting a starting material with a hydrogenation catalyst comprising a particulate nickel metal (Ni(0)) to hydrogenate the starting material, wherein the hydrogenation catalyst contains less than 1 wt % aluminum, wherein the particulate nickel metal is 95 wt % to 99.99 wt % nickel metal (Ni(0));
    wherein hydrogenation of the starting material comprises hydrogenation of an unsaturated compound, reductive alkylation of a carbonyl compound to an amine, hydrogenolysis of an ester or ether, dehydrogenation of a hydrocarbon or alcohol, dehalogenation, desulfurization, reduction of a nitro group to an amine group, reduction of a nitrile to an amine, reduction of an aldehyde to an alcohol, reduction of an olefin to a paraffin, reduction of an alkyne to a paraffin, reduction of an aromatic compound to an aliphatic compound, or a combination thereof.

2. The method of claim 1, wherein the hydrogenation of the starting material comprises hydrogenation of an unsaturated compound, reductive alkylation of a carbonyl compound to an amine, hydrogenolysis of an ester or ether, dehydrogenation of a hydrocarbon or alcohol, dehalogenation, desulfurization, or a combination thereof.

3. The method of claim 1, wherein the hydrogenation of the starting material comprises at least one of reduction of a nitro group to an amine group, reduction of a nitrile to an amine, reduction of an aldehyde to an alcohol, reduction of an olefin to a paraffin, reduction of an alkyne to a paraffin, and reduction of an aromatic compound to an aliphatic compound.

4. The method of claim 1, wherein the hydrogenation catalyst has a BET Specific Surface Area of about 2 $m^2/g$ to about 200 $m^2/g$, at least 10% of the particles of the hydrogenation catalyst have particle size (D10) of no greater than about 6 μm, and the hydrogenation catalyst has a sodium content less than about 1 wt %.

5. The method of claim 1, wherein the hydrogenation catalyst comprises nickel crystallites, wherein:
    the hydrogenation catalyst has a BET Specific Surface Area of at least about 1 $m^2/g$;
    at least 10% of the nickel crystallites have a size (C10) that is less than about 20 nm;
    the nickel crystallites have an average crystallite size of no greater than about 100 nm; and
    the nickel crystallite size distribution span is greater than about 1.0.

6. The method of claim 5, wherein the nickel crystallites have an average crystallite size of no greater than 20 nm to 25 nm.

7. The method of claim 1, wherein the particulate nickel metal (Ni(0)) has a BET SSA of 2 $m^2/g$ to 200 $m^2/g$.

8. The method of claim 1, wherein at least 10% of particles of the particulate nickel metal (Ni(0)) have a size (D10) of no greater than 6 μm.

9. The method of claim 1, wherein the hydrogenation catalyst has a sodium content less than 1 wt %.

10. The method of claim 1, wherein the hydrogenation catalyst is free-flowing.

11. The method of claim 1, wherein the particulate nickel metal (Ni(0)) has a sulfur content of 0.001 wt % to 5 wt %.

12. The method of claim 1, wherein the hydrogenation catalyst is made using a method comprising:
    calcining first nickel(II)-containing particles in an atmosphere comprising oxidizing constituents to generate second nickel(II)-containing particles; and
    reducing the second nickel(II)-containing particles in a reducing atmosphere while rotating or turning the second nickel(II)-containing particles at about 275° C. to about 360° C. for a time sufficient to generate the particulate nickel metal (Ni(0)), wherein the particulate nickel metal (Ni(0)) is free flowing.

13. The method of claim 12, wherein wither water nor steam are added to the educing atmosphere.

14. The method of claim 12, wherein a $H_2$:Ni molar ratio is employed during the reducing of between 1.0 and 2.5.

15. The method of claim 12, wherein a $H_2$/Ni molar ratio is employed during the reducing that is greater than about 2.

16. The method of claim 12, further comprising adding sulfur to the first nickel(II)-containing particles, the second nickel(II)-containing particles, or a combination thereof.

17. The method of claim 16, wherein the added sulfur is elemental sulfur.

18. The method of claim 12, wherein at the time of the calcining, the first nickel(II)-containing particles contain about 0.001 wt % to about 5 wt % sulfur, on a nickel basis. and/or wherein at the time of the reducing the second nickel(II)-containing particles contain about 0.001 wt % to about 5 wt % sulfur on a nickel basis.

19. The method of claim 12, wherein the reducing is performed in a rotary kiln processor.

20. The method of claim 16, wherein the particulate nickel metal is 98 wt % to 99.99 wt % nickel metal (Ni(0)).

* * * * *